(12) United States Patent
Davis, Jr.

(10) Patent No.: US 7,208,605 B2
(45) Date of Patent: Apr. 24, 2007

(54) FUNCTIONALIZED IONIC LIQUIDS, AND METHODS OF USE THEREOF

(75) Inventor: James Hillard Davis, Jr., Mobile, AL (US)

(73) Assignee: University of South Alabama, Mobile, AL (US)

( * ) Notice: Subject to any disclaimer, the term of this patent is extended or adjusted under 35 U.S.C. 154(b) by 418 days.

(21) Appl. No.: 10/407,473

(22) Filed: Apr. 4, 2003

(65) Prior Publication Data

US 2004/0035293 A1 Feb. 26, 2004

Related U.S. Application Data

(60) Provisional application No. 60/370,130, filed on Apr. 5, 2002.

(51) Int. Cl.
*C07D 231/00* (2006.01)
(52) U.S. Cl. ............... 548/110; 564/291; 564/295; 568/9; 568/10; 568/11
(58) Field of Classification Search ............... 548/110; 564/291, 295; 568/10, 11, 9
See application file for complete search history.

(56) References Cited

U.S. PATENT DOCUMENTS

| | | | |
|---|---|---|---|
| 4,761,164 A | 8/1988 | Pez et al. ............ 55/16 |
| 2002/0010291 A1* | 1/2002 | Murphy ............ 526/133 |

FOREIGN PATENT DOCUMENTS

JP 54079278 A * 6/1979

OTHER PUBLICATIONS

Fargo-Dubreuil et al., Catalysed Esterications in Room Temperature Ionic Liquids with Acidic Counteranion as Recyclable Reaction Media, Catalysis Communication, 3 2002, 185-190.*
Visser et al., Hydrophobic Ionic Liquids Incorporating N-alkylisoquinolinium Cations and their Utilization in Liquid-Liquid Separations, Chem Commun. 2001, 2484-2485.*
Welton, Room-Temperature Ionic Liquids. Solvents for Synthesis and Catalysis, Chem. Rev. 1999, 99, 2071-2083.*

(Continued)

*Primary Examiner*—Thurman Page
*Assistant Examiner*—Chukwuma Nwaonicha
(74) *Attorney, Agent, or Firm*—Dana M. Gordon; Foley Hoag LLP

(57) ABSTRACT

One aspect of the present invention relates to ionic liquids comprising a pendant Bronsted-acidic group, e.g., a sulfonic acid group. Another aspect of the present invention relates to the use of an ionic liquid comprising a pendant Bronsted-acidic group to catalyze a Bronsted-acid-catalyzed chemical reaction. A third aspect of the present invention relates to ionic liquids comprising a pendant nucleophilic group, e.g., an amine. Still another aspect of the present invention relates to the use of an ionic liquid comprising a pendant nucleophilic group to catalyze a nucleophile-assisted chemical reaction. A fifth aspect of the present invention relates to the use of an ionic liquid comprising a pendant nucleophilic group to remove a gaseous impurity, e.g., carbon dioxide, from a gas, e.g., sour natural gas.

24 Claims, 1 Drawing Sheet

Table. Analysis of Octyl Ether Formation.

| Entry | Sulfonic Acid Derivative | Ratio of 1-octanol to sulfonic acid derivative | Ratio of 1-octanol to octyl ether[a] | Isolated Yield, % |
|---|---|---|---|---|
| 1 | 2a | 2.2:1.0 | 54:46 | 25 |
| 2 | 2a | 3.3:1.0 | 20:80 | 56 |
| 3 | 2a | 5.0:1.0 | 77:23 | 16 |
| 4 | 3 | 2.2:1.0 | 15:85 | 49 |
| 5 | 4 | [b] | 96:4 | 3 |

[a]Ratio based upon unreacted 1-octanol to isolated octyl ether (GC analysis of the distilled product). [b]0.28 meq which is based upon amount of 1-octanol (0.5 mL, 3.17 mmol) and NAFION (314 mg, 0.28 meq (0.89 meq/g)) used.

OTHER PUBLICATIONS

Visser et al., Task-specific ionic liquids for the extraction of metal ions from aqueous Solutions, Chem Commun. 2001, 135-136.*

Bates et al., CO2 Capture by a Task-Specific Ionic Liquid, J. Am. Chem. Soc., 124, 6, 2002, 926-927.*

Merrigan et al., New Fluorous Ionic Liquids Function as Surfactants in Conventional Room-Temperature Ionic Liquids, Chem Commun. 2001, 2051-2052.*

Frago-Dubreuil et al., Grafted Ionic Liquid-Phase-Supported Synthesis of Small Organic Molecules, Tetrahedron Letters 42 (2001) 6097-6100.*

Branco et al., Ionic Liquid as Recyclable Reaction Media for the Tetrahydropyranylation of Alcohols, Tetrahedron 57 (2001) 4405-4410.*

International Search Report, PCT US03/10318 Application, mailed Apr. 15, 2004.

Lundberg, et al., "Gem-Dibasic Ligands With Phosphorus, Sulfur, and Nitrogen Sites and Some Boron Derivatives", Univ. of South Dakota, Vermillion, SD., USA, Inorganic Chemistry (1969), 8 (6), 1336-40.

Sugimoto, et al., "Preparation Of Some Unsymmetrical Methylenedionium Salts and Their Reaction With Nucleophiles", Inst. Chem. Res., Kyoto Univer., Uji, Japan, Bulletin of the Inst. For Chem. Research, Kyoto University (1982), 60 (5-6), 302-8.

Wedgwood, et al., "Water Soluble Platinum (II) and Palladium (II) Complexes Of Alkyl Sulfonated Phosphines", Chem. Divis., Staffordshire University, Stoke-on-Trent, ST4, 2DE, UK, Inorganica Chimica Acta (1999), 290 (2), 189-196.

Gosselck, et al., "Dialkyl (Triphenylphosphoniomethyl) Sulfonium Bissalts and Their Conversion Into Stable Ylide Salts", Unvi. Giessen, Giessen, Fed. Rep. Ger., Angewandte Chemie, Intern'l Edition in Engl. (1967), 6(3), 249.

Abbott et al.; "Preparation of Novel, Moisture-stable, Lewis-acidic Ionic Liquids Containing Quaternary Ammonium Salts with Functional Side Chains", Chem. Commun., 2010-2011, (2001).

Bates et al.; "$CO_2$ Capture by a Task-Specific Ionic Liquid", J. Am. Chem. Soc., 124(6): 926-927, (2002).

Branco and Afonso; "Ionic Liquids as Recycable Reaction Media for the Tetrahydropyranylation of Alcohols", Tetrahedron 57: 4405-4410, (2001).

Crich and Neelamkavil, "Fluorous Swern Reaction", J. Am. Chem. Soc. 123: 7449-7450, (2001).

Cole et al.; "Novel BrØnsted Acidic Ionic Liquids and their Use as Dual Solvent Catalysts", J. Am. Chem. Soc. 124: 5962-5963, (2002).

Davis, Jr. and Forrester; "Thiazolium-ion Based Organic Ionic Liquids (OILs).$^{1,2}$ Novel OILs which promote the Benzoin Condensation",Tetrahedron Letters 40: 1621-1622, (1999).

Davis, Jr. et al.; "Novel Organic Ionic Liquids (OILs) Incorporating Cations Derived from the Antifungal Drug Miconazole", Tetrahedron Letters 39: 8955-8958, (1998).

Egashira et al.; "The Effect of the Coexistence of Anion Species in Imidazolium Cation-based Molten Salt Systems", Solid State Ionics 148:457-461, (2002).

Fraga-Dubreuil et al.; "Catalysed Esterifications in Room Temperature Ionic Liquids with Acidic Counteranion as Recyclable Reaction Media", Catalysis Communications 3: 185-190, (2002).

Fraga-Dubreuil and Bazureau; "Grafted Ionic Liquid-phase-Supported Synthesis of Small Organic Molecules", Tetrahedron Letters 42: 6097-6100, (2001).

Manabe Kei; "Synthesis of Novel Chiral Quaternary Phosphonium Salts with a Multiple Hydrogen-Bonding Site, and their Application to Asymmetric Phase-Transfer Alkylation", Tetrahedron 54:14465-14476, (1998).

Merrigan et al.; "New Fluorous Ionic Liquids Functions as Surfactants in Conventional Room -temperature Ionic Liquids", Chem. Commun. 2051-2052, (2000).

Neimann and Neumann; "Electrophilic Activation of Hydrogen Peroxide: Selective Oxidation Reactions in Perfluorinated Alcohol Solvents", Organic Letters, 2(18): 2861-2863, (2000).

Neimann and Neumann; "A New Non-metal Heterogeneous Catalyst for the Activation of Hydrogen Peroxide: A Perfluorinated Keton Attached to Silica for Oxidation of Aromatic Amines and Alkenes", Chem. Commun. pp. 487-488, (2001).

Nishide et al.; "New Odorless Protocols for the Swern and Corey-Kim Oxidations", Tetrahedron Letters 43:5177-5179, (2002).

Quinn et al.; "Polyelectrolyte-Salt Blend Membranes for Acid Gas Separations", Journal of Membrane Science 131: 61-69, (1997).

Quinn et al.; "New Facilitated Transport Membranes for the Separation of Carbon Dioxide from Hydrogen and Methane", Journal of Membrane Science 104: 139-146, (1995).

Ullrich et al.; "Lithium Salts of Bis (Perfluoroalkyl) Sulfonic Acids: Synthesis, Characterization and Conductivity Studies", Journal of Fluorine Chemistry, 79: 33-38, (1996).

Van Vliet et al.; "Perfluoroheptadecan-9-one: A Selective and Reusable Catalyst for Epoxidations with Hydrogen Peroxide", Chem. Commun. pp. 263-264, (1999).

Visser et al.; "Hydrophobic Ionic Liquids Incorporating N-Alkylisoquinolinium Cations and their Utilization in Liquid-Liquid Separations", Chem. Commun. pp. 2484-2485, (2001).

Visser et al.; "Task-Specific Ionic Liquids for the Extraction of Metal Ions from Aqueous Solutions", Chem. Commun. pp. 135-136, (2001).

Wassersheid et al.; "Synthesis and properties of ionic Liquids Derived from the 'Chiral Pool'", Chem. Commun. pp. 200-201, (2002).

Welton Thomas; "Room-Temperature Ionic Liquids. Solvents for Synthesis and Catalysis", Chem. Rev. 99: 2071-2083, (1999).

Yoshizawa et al.;, "Ion Conduction in Zwitterionic-type Molton Salts and their Polymers", J. Matter. Chem. 11: 1057-1062, (2001).

Yao and Richardson; "Epoxidation of Alkenes with Bicarbonate-Activated Hydrogen Peroxide", J. Am. Chem. Soc. 122:3220-3221, (2000).

* cited by examiner

Table. Analysis of Octyl Ether Formation.

| Entry | Sulfonic Acid Derivative | Ratio of 1-octanol to sulfonic acid derivative | Ratio of 1-octanol to octyl ether[a] | Isolated Yield, % |
|---|---|---|---|---|
| 1 | 2a | 2.2:1.0 | 54:46 | 25 |
| 2 | 2a | 3.3:1.0 | 20:80 | 56 |
| 3 | 2a | 5.0:1.0 | 77:23 | 16 |
| 4 | 3 | 2.2:1.0 | 15:85 | 49 |
| 5 | 4 | _[b] | 96:4 | 3 |

[a]Ratio based upon unreacted 1-octanol to isolated octyl ether (GC analysis of the distilled product). [b]0.28 meq which is based upon amount of 1-octanol (0.5 mL, 3.17 mmol) and NAFION (314 mg, 0.28 meq (0.89 meq/g)) used.

FUNCTIONALIZED IONIC LIQUIDS, AND METHODS OF USE THEREOF

RELATED APPLICATIONS

This application claims the benefit of priority to U.S. Provisional Patent Application Ser. No. 60/370,130, filed Apr. 5, 2002.

BACKGROUND OF THE INVENTION

Ionic Liquids

Room temperature ionic liquids consist of ions. However, unlike conventional molten salts (for example, molten sodium chloride), these materials often melt below 100° C. Since the melting points are low, ionic liquids can act as solvents in which reactions can be performed, and because the liquid is made of ions rather than molecules, such reactions often provide distinct selectivities and reactivities as compared to conventional organic solvents.

Room-temperature ionic liquids have been used as clean solvents and catalysts for green chemistry and as electrolytes for batteries, photochemistry and electrosynthesis. They have no significant vapor pressure and thus create no volatile organic contaminants. They also allow for easy separation of organic molecules by direct distillation without loss of the ionic liquid. Their liquid range can be as large as 300° C. allowing for large reaction kinetic control, which, coupled with their good solvent properties, allows small reactor volumes to be used. Salts based upon poor nucleophilic anions, such as $[BF_4]^-$, $[PF_6]^-$, $[CF_3CO_2]^-$, and $[CF_3SO_3]^-$, are water and air insensitive and possess remarkably high thermal stability. Many of these materials are based around an imidazolium cation, 1-alkyl-3-methylimidazolium. By changing the anion or the alkyl chain on the cation, a wide variation in properties, such as hydrophobicity, viscosity, density and solvation, can be obtained. For example, ionic liquids will dissolve a wide range of organic molecules to an appreciable extent, the solubility being influenced by the nature of the counter anion.

The unique physical properties of ionic liquids have been found to offer certain advantages in numerous applications. For example, U.S. Pat. No. 5,827,602 to Koch et al. discloses ionic liquids having improved properties for application in batteries, electrochemical capacitors, catalysis, chemical separations, and other uses. The ionic liquids described in Koch et al. are hydrophobic in nature, being poorly soluble in water, and contain only non-Lewis acid anions. When fluorinated, they were found to be particularly useful as hydraulic fluids and inert liquid diluents for highly reactive chemicals. In addition, ionic liquids have been discussed by Freemantle, M. Chem. Eng. News 1998, 76 [March 30], 32; Carmichael, H. Chem. Britain, 2000, [January], 36; Seddon, K. R. J. Chem. Tech. Biotechnol. 1997, 68, 351; Welton, T. Chem. Rev. 1999, 99, 2071; Bruce, D. W., Bowlas, C. J., Seddon, K. R. Chem. Comm. 1996, 1625; Merrigan, T. L., Bates, E. D., Dorman, S. C., Davis, J. H. Chem. Comm. 2000, 2051; Freemantle, M. Chem. Eng. News, 2000, 78 [May 15], 37. See also Holbrey, J. D.; Seddon, K. R. Clean Products and Processes 1999, 1, 223–236; and Dupont, J., Consorti, C. S. Spencer, J. J Braz. Chem. Soc. 2000, 11, 337–344.

Ionic liquids have been disclosed for use as solvents for a broad spectrum of chemical processes. These ionic liquids, which in some cases can serve as both catalyst and solvent, are attracting increasing interest from industry because they promise significant environmental benefits, e.g., because they are nonvolatile they do not emit vapors. Hence, for example, they have been used in butene dimerization processes. WO 95/21871, WO 95/21872 and WO 95/21806 relate to ionic liquids and their use to catalyse hydrocarbon conversion reactions such as polymerisation and alkylation reactions. The ionic liquids described for this process were preferably 1-($C_1$–$C_4$ alkyl)-3-($C_6$–$C_{30}$ alkyl) imidazolium chlorides and especially 1-methyl-3-$C_{10}$ alkyl-imidazolium chloride, or 1-hydrocarbyl pyridinium halides, where the hydrocarbyl group is, for example, ethyl, butyl or other alkyl. PCT publication WO 01/25326 to Lamanna et al. discloses an antistatic composition comprising at least one ionic salt consisting of a nonpolymeric nitrogen onium cation and a weakly coordinating fluoroorganic anion, the conjugate acid of the anion being a superacid, in combination with thermoplastic polymer. The composition was found to exhibit good antistatic performance over a wide range of humidity levels.

Bronsted Acid Catalysis

From undergraduate laboratories to chemical manufacturing plants, the use of strong Bronsted acids is ubiquitous. Smith, M. B.; March, J. *March's Advanced Organic Chemistry*; Wiley-Interscience: New York, 2001; Chapter 8. In this context, solid acids are being more widely used since, as non-volatile materials, they are deemed less noxious than traditional liquid acids. Ritter, S. K. *Chem. Eng. News*, 2001, 79 (40), 63–67. However, solid acids have shortcomings. Among the more troublesome of these are restricted accessibility of the matrix-bound acidic sites, high mw/active site ratios, and rapid deactivation from coking. Ishihara, K.; Hasegama, A. and Yamamoto, H. *Angew. Chem. Int. Ed.*, 2001, 40, 4077–4079; and Harmer, M. A. and Sun, Q. *Appl. Catal. A: General*, 2001, 221, 45–62.

Bearing in mind both the advantages and disadvantages of solid acids, the search continues for systems that are Bronsted acids with solid-like non-volatility but that manifest the motility, greater effective surface area and potential activity of a liquid phase. Combining just these characteristics, ionic liquids (IL) have been described as one of the most promising new reaction mediums. Seddon, K. R. *J. Chem. Technol. Biotechnol.* 1997, 68, 351–356. Not only can these unusual materials dissolve many organic and inorganic substrates, they are also readily recycled and are tunable to specific chemical tasks. Bates, E. D.; Mayton, R. D.; Ntai, I. and Davis, J. H. Jr. *J. Am. Chem Soc.* 2002, 124, 926–927; Visser, A. E.; Holbrey, J. D.; Rogers, R. D. *Chem. Commun.*, 2001, 2484–2485; Visser, A. E.; Swatloski, R. P.; Reichert, W. M.; Mayton, R.; Sheff, S.; Wierzbicki, A.; Davis, J. H. Jr.; Rogers. R. D. *Chem. Commun.*, 2001, 135–136; Merrigan, T. L.; Bates, E. D.; Dorman; S. C.; Davis, J. H. Jr. *Chem. Commun.* 2000, 2051–2052; Forrester, K. J.; Davis, J. H. Jr. *Tetrahedron Lett.*, 1999, 40, 1621–1622; and Morrison, D. W.; Forbes D. C.; Davis, J. H. Jr. *Tetrahedron Letters*, 2001, 42, 6053–6057.

Further, the chemical industry is under significant pressure to replace the volatile organic compounds that are currently used as solvents in organic synthesis. Many of these solvents, such as chlorinated hydrocarbons, are toxic and hazardous for the environment, due to their emissions in the atmosphere and the contamination of aqueous effluents. Ionic liquids (IL) seem to offer a solution to this problem, too. Ionic liquids have no measurable vapor pressure. This means that they don't evaporate, and therefore they emit no hazardous vapors in the atmosphere, and replenishing of the solvent is not required. This property also allows easy separation of volatile products. ILs are able to dissolve a wide range of organic, inorganic and organometallic compounds. Notably, their properties can be adjusted by altering the cation or anion of the IL, allowing for fine tuning of the reaction.

Moreover, many organic transformations, such as Fischer esterification, alcohol dehydrodimerization and the pinacol/benzopinacole rearrangement, require an acidic catalyst. Solid acids are now being used since, as nonvolatile compounds, they are less hazardous than traditional liquid acids. As noted above, although they are less hazardous, solid acids have several disadvantages, such as restricted accessibility of the matrix-bound acidic sites, high molecular weight/active-site ratios, and rapid deactivation from coking. Cole, A. C.; Jensen, J. L.; Ntai, I.; Tran, K. L. T.; Weaver, K. J.; Forbes, D. C.; Davis, J. H., Jr. *J. Am. Chem. Soc.* 2002, 124, 5962–5963.

Purification of Gas Mixtures

There is little doubt that petroleum, coal and natural gas will continue to be the primary global fuel and chemical feedstock sources for some years to come. Mills, Mark P. *Energy Policy in the Electron Age,* Mills-McCarthy & Associates, Inc. http://www.fossilfuels.org/electric/electron.htm. Natural gas is regarded as the cleanest of these materials, and as such is being consumed at an accelerating pace. Despite its reputation as a clean fuel, natural gas is usually contaminated with a variety of undesirable materials, especially $CO_2$ and $H_2S$. While this level of contamination is very low in gas from certain sources (sweet gas), it is much higher in gas from others (sour gas). As sweet gas reserves are depleted, pressures will build for the increased utilization of sour gas. *Oil and Gas R&D Programs: Securing the U.S. Energy, Environmental and Economic Future.* Office of Fossil Energy, U.S. Dept. of Energy, Office of Natural Gas and Petroleum Technology: Washington, D.C., 1997. Since admixed $CO_2$ lowers the fuel value of natural gas, the large amount of it present in sour gas compels its removal prior to combustion. The lower fuel value for sour gas, coupled with the connection between $CO_2$ and global warming, makes $CO_2$ capture a commercially important and environmentally desirable process.

One of the most attractive approaches for the separation of a target compound from a mixture of gases in a gas stream is selective absorption into a liquid. Astarita, G,; Savage, D. W.; Bisio, A. *Gas Treating with Chemical Solvents;* Wiley-Interscience: New York, 1983. Such interactions between gases and pure liquids or solutions are the bases for numerous gas separation technologies, including commercial systems for the removal of $CO_2$ from natural gas. These scrubbing processes include ones in which the simple, differential dissolution of the target gas into the liquid phase is of principal importance. More common are processes in which a chemical reaction of the target gas with a solute in the liquid phase is the main mode of sequestration. With either mode of gas removal, the vapor pressure of the solvent itself plays a significant role in gas-liquid processes, usually to their detriment. In the case of large-scale $CO_2$ capture, aqueous amines are used to chemically trap the $CO_2$ by way of ammonium carbamate formation. In these systems, the uptake of water into the gas stream is particularly problematic. Compounding the water uptake difficulty is the loss into the gas stream of the volatile amine sequestering agent.

A liquid that could facilitate the sequestration of gases without concurrent loss of the capture agent or solvent into the gas stream should prove to be a superior material in such applications. To this end, ionic liquids (low temperature molten salts) have been proposed as solvent-reagents for gas separations. Pez, G. P.; Carlin, R. T.; Laciak, D. V.; Sorensen, J. C. U.S. Pat. No. 4,761,164. Due to the coulombic attraction between the ions of these liquids, they exhibit no measurable vapor pressure up to their thermal decomposition point, generally >300° C. This lack of vapor pressure makes these materials highly attractive for gas processing. Indeed, for these purposes they may be thought of as "liquid solids," incorporating some of the most useful physical properties of both phases.

Despite the general promise of ionic liquids (IL) in gas treatment, the molten salts used thus far for $CO_2$ separation are generally "off the shelf" materials, such as $(CH_3)_4NF$ tetrahydrate, that are not optimized for this purpose, frequently depending upon another volatile reagent, water. Pez, G. P.; Carlin, R. T.; Laciak, D. V.; Sorensen, J. C. U.S. Pat. No. 4,761,164; Quinn, R.; Pez, G P. U.S. Pat. No. 4,973,456; and Quinn, R.; Appleby, J. B.; Pez, G. P. *J. Am. Chem. Soc.,* 1995, 117, 329. For instance, the latter salt uses the very weakly basic bifluoride ion to drive the net generation of bicarbonate from $CO_2$ and water.

The prospects for preparing a broad array of ionic liquids with ions incorporating functional groups are good. Freemantle, M. *Chemical & Engineering News,* May 15, 2000, 37. Moreover, certain of these new "task-specific" ionic liquids have proven useful in both synthetic and separations applications. Visser, A. E.; Holbrey, J. D.; Rogers, R. D. *Chem. Commun.,* 2001, 2484; Visser, A. E.; Swatloski, R. P.; Reichert, W. M.; Mayton, R.; Sheff, S.; Wierzbicki, A.; Davis, J. H. Jr.; Rogers. R. D. *Chem. Commun.,* 2001, 135; Merrigan, T. L.; Bates, E. D.; Dorman; S. C.; Davis, J. H. Jr. *Chem. Commun.* 2000, 2051; Fraga-Dubreuil, J.; Bazureau J. P. *Tetrahedron Lett.,* 2001, 42, 6097; and Forrester, K. J.; Davis, J. H. Jr. *Tetrahedron Lett.,* 1999, 40, 1621.

SUMMARY OF THE INVENTION

In certain embodiments, the present invention relates to a salt represented by 1:

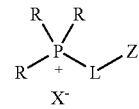

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$SO_3H$, —$CO_2H$, —$CO_2R$, —$C(O)N(R")_2$, —$C(O)N(R")N(R")_2$, —$N(R')_2$, —OR', —SR', —$S(O)R"$, —$S(O)_2R"$, —CN, —$N(R")P(O)(R)_2$, —$C(OR')(R")_2$, alkenyl, or alkynyl;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a salt represented by 2:

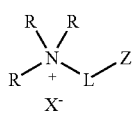

2 wherein

R represents independently for each occurrence alkyl, fluoroalkyl, cycloalkyl, aryl, heteroaryl, aralkyl, heteroaralkyl, or —(CH$_2$)$_n$—R$_8$; or ⁺NR$_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R³ represents independently for each occurrence H, F, or alkyl;

L represents (C(R³)$_2$)$_n$, (C(R³)$_2$)$_n$J(C(R³)$_2$)$_m$, or (C(R³)$_2$)$_n$Ar(C(R³)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a salt represented by 3:

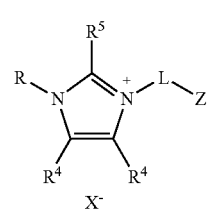

3 wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R³ represents independently for each occurrence H, F, or alkyl;

R⁴ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R⁵ represents independently for each occurrence H, alkyl, fluoroalkyl, aryl, heteroaryl, aralkyl, heteroaralkyl, or —(CH$_2$)$_n$—R$_8$;

L represents (C(R³)$_2$)$_n$, (C(R³)$_2$)$_n$J(C(R³)$_2$)$_m$, or (C(R³)$_2$)$_n$Ar(C(R³)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a method of removing carbon dioxide, carbonyl sulfide, sulfur dioxide, sulfur trioxide, hydrogen sulfide or a carbonyl-containing compound from a gaseous or liquid mixture, comprising the step of exposing a gaseous or liquid mixture to a salt selected from the group consisting of:

salts represented by 1:

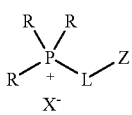

1 wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

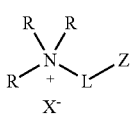

2 wherein

R represents independently for each occurrence alkyl, fluoroalkyl, cycloalkyl, aryl, heteroaryl, aralkyl, heteroaralkyl, or —$(CH_2)_n$—$R_8$; or $^+NR_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

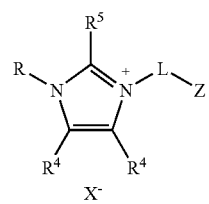

3 wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

R⁴ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R⁵ represents independently for each occurrence H, alkyl, fluoroalkyl, aryl, heteroaryl, aralkyl, heteroaralkyl, or —$(CH_2)_n$—$R_8$;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R'')_2$;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a method of transporting carbon dioxide, carbonyl sulfide, sulfur dioxide, sulfur trioxide, hydrogen sulfide or a carbonyl-containing compound from a first gaseous or liquid mixture to a second gaseous or liquid mixture, comprising the step of exposing a first gaseous or liquid mixture to a salt selected from the group consisting of:

salts represented by 1:

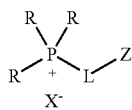

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R'' represents independently for each occurrence H, alkyl, fluoroalkyl, aryl, heteroaryl, aralkyl, heteroaralkyl, or —$(CH_2)_n$—$R_8$;

R³ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R'')_2$;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

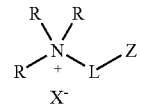

wherein

R represents independently for each occurrence alkyl, fluoroalkyl, cycloalkyl, aryl, heteroaryl, aralkyl, heteroaralkyl, or —$(CH_2)_n$—$R_8$; or ⁺$NR_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R'' represents independently for each occurrence H, alkyl, fluoroalkyl, aryl, heteroaryl, aralkyl, heteroaralkyl, or —$(CH_2)_n$—$R_8$;

R³ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R'')_2$;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

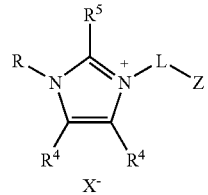

wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

R$^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R$^5$ represents independently for each occurrence H, alkyl, fluoroalkyl, aryl, heteroaryl, aralkyl, heteroaralkyl, or —(CH$_2$)$_n$—R$_8$;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —N(R')$_2$, —OR', —SR', or —C(OR')(R")$_2$;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and exposing subsequently said salt to a second gaseous or liquid mixture, thereby transporting carbon dioxide, carbonyl sulfide, sulfur dioxide, sulfur trioxide, hydrogen sulfide or a carbonyl-containing compound to said second gaseous or liquid mixture.

In certain embodiments, the present invention relates to a method of removing an alkene, alkyne or carbon monoxide from a mixture, comprising the step of exposing a mixture to a complex formed from a transition metal and a salt selected from the group consisting of:

salts represented by 1:

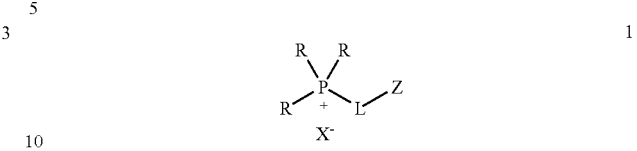

wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$^8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

wherein

R represents independently for each occurrence alkyl, fluoroalkyl, cycloalkyl, aryl, heteroaryl, aralkyl, heteroaralkyl, or —(CH$_2$)$_n$—R$_8$; or $^+$NR$_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

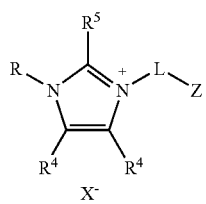

3 wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

R$^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R$^5$ represents independently for each occurrence H, alkyl, fluoroalkyl, aryl, heteroaryl, aralkyl, heteroaralkyl, or —(CH$_2$)$_n$—R$_8$;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a method of catalyzing an acid-catalyzed chemical reaction to give a product, comprising the step of exposing a reactant mixture to a salt selected from the group consisting of:

salts represented by 1:

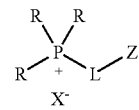

1 wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H or —CO$_2$H;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

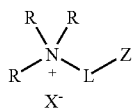

2 wherein

R represents independently for each occurrence alkyl, fluoroalkyl, cycloalkyl, aryl, heteroaryl, aralkyl, heteroaralkyl, or —(CH$_2$)$_n$—R$_8$; or ⁺NR$_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

$R^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H or —CO$_2$H;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

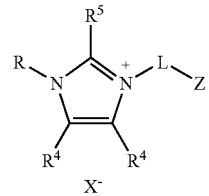

3 wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

$R^3$ represents independently for each occurrence H, F, or alkyl;

$R^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

$R^5$ represents independently for each occurrence H, alkyl, fluoroalkyl, aryl, heteroaryl, aralkyl, heteroaralkyl, or —(CH$_2$)$_n$—R$_8$;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H or —CO$_2$H;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a method of catalyzing a base-catalyzed chemical reaction to give a product, comprising the step of exposing a reactant mixture to a salt selected from the group consisting of:

salts represented by 1:

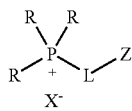

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

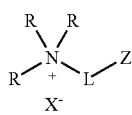

wherein

R represents independently for each occurrence alkyl, fluoroalkyl, cycloalkyl, aryl, heteroaryl, aralkyl, heteroaralkyl, or —$(CH_2)_n$—$R_8$; or $^+NR_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

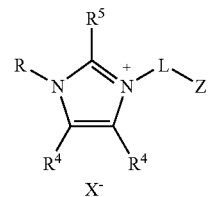

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

$R^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

$R^5$ represents independently for each occurrence H, alkyl, fluoroalkyl, aryl, heteroaryl, aralkyl, heteroaralkyl, or —$(CH_2)_n$—$R_8$;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a method of preparing a solution, comprising the step of combining a solute and a solvent to produce a solution, wherein said solvent is selected from the group consisting of:

salts represented by 1:

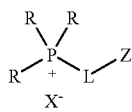

1 wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$SO_3H$, —$CO_2H$, —$CO_2R$, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

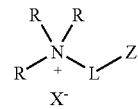

2 wherein

R represents independently for each occurrence alkyl, fluoroalkyl, cycloalkyl, aryl, heteroaryl, aralkyl, heteroaralkyl, or —$(CH_2)_n$—$R_8$; or $^+NR_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$SO_3H$, —$CO_2H$, —$CO_2R$, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

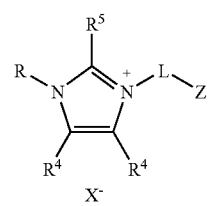

3 wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

$R^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

$R^5$ represents independently for each occurrence H, alkyl, fluoroalkyl, aryl, heteroaryl, aralkyl, heteroaralkyl, or —$(CH_2)_n$—$R_8$;

L represents $(C(R^3)_2)_n$, $(C(R')_2)_n J(C(R^3)_2)_m$, or $(C(R^3)_2)_n AR(C(R^3)_2)_m$;

Z represents —$SO_3H$, —$CO_2H$, —$CO_2R$, —$C(O)N(R")_2$, —$C(O)N(R")N(R")_2$, —$N(R')_2$, —OR', —SR', —$S(O)R"$, —$S(O)_2R"$, —CN, —$N(R")P(O)(R)_2$, —$C(OR')(R")_2$, alkenyl, or alkynyl;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

DETAILED DESCRIPTION OF THE INVENTION

Figure 1:
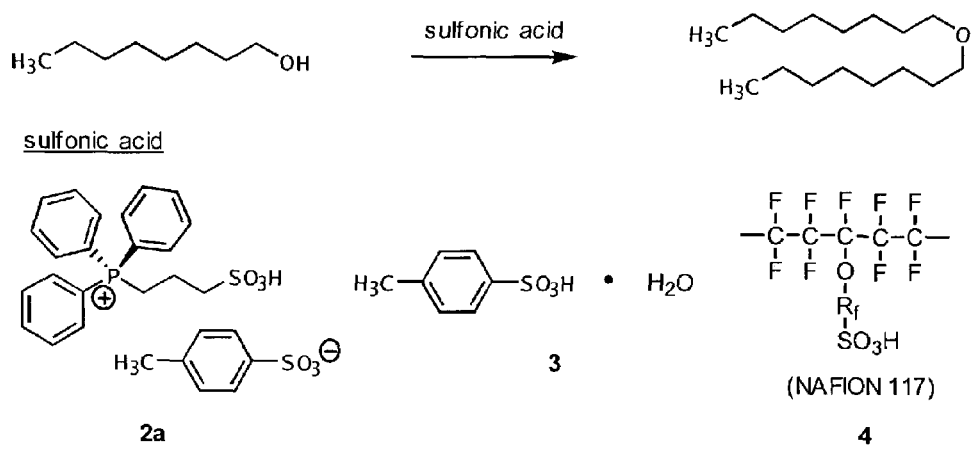
FIG. 1 depicts and tabulates the yields for the formation of n-octyl ether from n-octanol catalyzed by triphenyl(propyl-3-sulphonyl)phosphonium toluenesulfonate, toluenesulfonic acid or Nafion® 117.

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Overview of Two Preferred Embodiments

The reaction of triphenylphosphine or N-butylimidazole with cyclic sultones gives zwitterions that are subsequently converted into ionic liquids by reaction with trifluoromethane sulfonic acid or p-toluene sulfonic acid. The resulting ionic liquids have cations to which are tethered alkane sulfonic acid groups. These Bronsted acidic ionic liquids are useful solvent/catalysts for several organic reactions, including Fischer esterification, alcohol dehydrodimerization and the pinacol rearrangement. The ionic liquids combine the low volatility and ease of separation from product normally associated with solid acid catalysts, with the higher activity and yields normally found using conventional liquid acids.

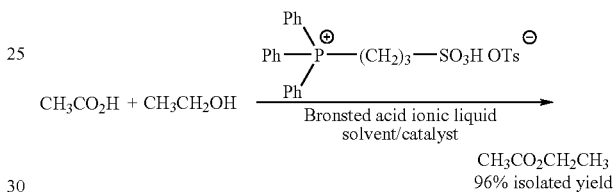

Reaction of 1-butyl imidazole with 3-bromopropylamine hydrobromide, followed by work-up and anion exchange, yields a room-temperature ionic liquid incorporating a cation with an appended amine group. The ionic liquid reacts reversibly with $CO_2$, reversibly sequestering the gas as a carbamate salt. The ionic liquid, which can be repeatedly recycled in this role, is comparable in efficiency for $CO_2$ capture to commercial amine sequestering reagents, and yet is non-volatile and does not require water in order to function.

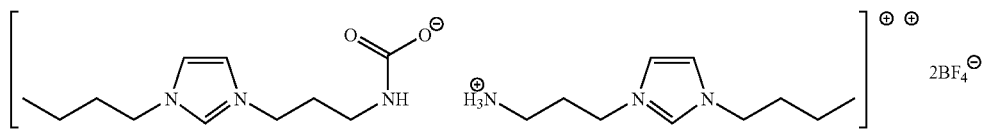

Bronsted Acidic Ionic Liquids and Their Use as Dual Sovents-Catalysts

Remarkably, we have developed the first ionic liquids that are strong Bronsted acids. Olivier-Bourbigou, H. and Magna, L. *J. Mol. Cat. A: Chemical*, 2002, 3484, 1–19; Cole, A. C.; Jensen, J. L.; Ntai, I.; Tran, K. L. T.; Weaver, K. J.; Forbes, D. C.; Davis, J. H., Jr. *J. Am. Chem. Soc.* 2002, 124, 5962–5963; and Welton, T. *Chem. Rev.* 1999, 99, 2071–2084. In each IL, an alkane sulfonic acid group is covalently tethered to the IL cation.

The synthetic approach used to assemble the zwitterionic precursors to the acidic IL is well-precedented. Reaction of the neutral nucleophiles N-butyl imidazole or triphenylphosphine with 1,4-butane sultone or 1,3-propane sultone, respectively, produces the requisite zwitterions in excellent yields. See Yoshizawa, M.; Hirao, M.; Ito-Akita, K. and Ohno, H. *J. Mater. Chem.* 2001, 11, 1057–1062. In the second step, the simultaneous realization of the latent acidity of the zwitterions and their conversion into ionic liquids is accomplished. The chemical yields for both the zwitterion formation and acidification steps are essentially quantitative. Moreover, since neither reaction produces by-products, the IL syntheses are 100% atom efficient.

The zwitterion acidification is accomplished by combining 1:1 molar quantities of the zwitterions with an acid possessing a $pK_a$ sufficiently low to convert the pendant sulfonate group into an alkane sulfonic acid, the $pK_a$ of the latter being ~–2. The result is the transformation of the zwitterion into an IL cation bearing an appended sulfonic acid group, with the conjugate base of the exogenous acid becoming the IL anion. Because these systems contain two formal negative charges per acidic proton, they may be regarded as internally self-buffered. For the IL syntheses reported here, the donor acids included trifluoromethane sulfonic acid, p-toluene sulfonic acid hydrate ($pTSA.H_2O$), sulfuric acid, $HPF_4$, $HPF_6$, and $(CF_3S(O)_2)_2NH$. Two acids were then used to convert zwitterions 1 and 2 to IL 1a and 2a, respectively. The acidifications were accomplished by stirring together the neat reagents and warming gently for 2–24 h.

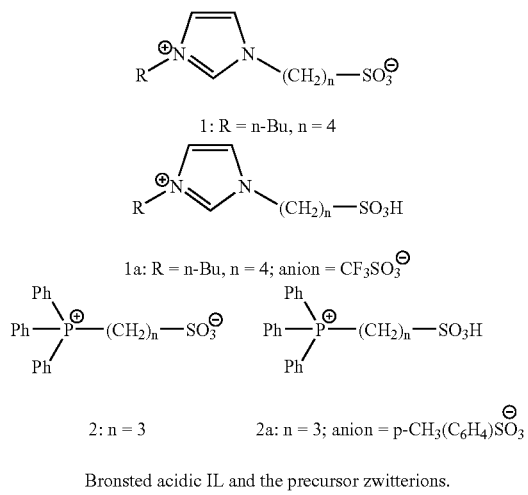

Bronsted acidic IL and the precursor zwitterions.

The IL 1a is a somewhat viscous liquid at room temperature, while 2a is a stiff glass that liquefies around 80° C. In keeping with the behavior of other IL, neither 1a or 2a fumes or manifests any observable degree of vapor pressure, unlike strong acids dissolved in conventional IL, which frequently continue to emit noxious vapors. Further, treatment of 1a under vacuum (10 torr) at 150° C. results in no observed loss of triflic acid ($CF_3SO_3H$ bp=162° C. @ 760 torr) from the IL. Moreover, washing 2a with toluene or diethyl ether results in no extraction of free pTSA (soluble in either liquid). Both of these behaviors are consistent with the donor acids being fully incorporated into their respective IL structures, rather than remaining simply mixtures of added strong acid with dissolved zwitterion, in which case some retention of pre-mixing characteristics (e.g., triflic acid volatility) would be expected.

Both new IL were screened as solvent/catalysts for several classical acid-promoted organic reactions, though we placed an emphasis upon probing the chemistry of 2a (vide infra). The reaction types screened were Fischer esterification, alcohol dehydrodimerization and the pinacol/benzopinacole rearrangement. Reactions and results are outlined below in Scheme 1.

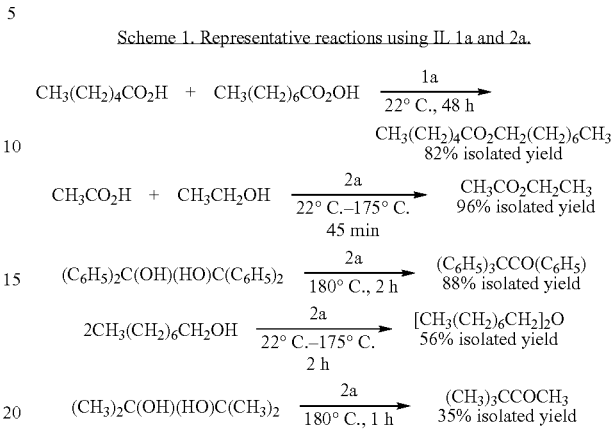

Both new ionic liquids proved catalytically active in these reactions. However, we placed an emphasis at this early stage of our studies upon more fully probing the chemistry of 2a. Our motivation for doing so originates in recent reports by Karodia and co-workers in which tetraorganophospbonium tosylate salts (mp>70° C.) were used as solvents for several organic reactions. Karodia, N.; Ludley, P. *Tetrahedron Lett.* 2001, 42, 2011–2014; Karodia, N.; Guise, S.; Newlands, C.; Andersen, J. *Chem. Commun.* 1998, 2341–2342; and Comyns, C.; Karodia, N.; Zeler, S.; Andersen, J. *Catal. Lett.* 2000, 67, 113–115. In those reports, the cooling of the solvent upon completion of the reaction resulted in the separation of the IL as a solid. We reasoned that 2a might behave similarly, providing direct access to a convenient mode of separation, decantation, which parallels the manner in which solid acids are removed from reaction media. As expected, this proved to be the case in most of the reactions in which 2a was used.

The reaction of alcohols with strong acids is used both for alkene and ether synthesis, the favored product being selected by the judicious choice of acid and reaction conditions. Depending upon the substrate/2a stoichiometry, 1-octanol is selectively converted to octyl ether in 16%–56% isolated yield with minimal by-product formation. In a control experiment, pTSA.H₂O gave a better yield of octyl ether but more by-products were formed and the separation of the pTSA from the reaction milieu was considerably more difficult. Using Nafion-117♦ as a control, we found the catalyst/product separation to be straightforward and by-product formation to be minimal, but the yield of octyl ether was quite poor (3%).

The rearrangement of pinacol to pinacolone is a process of considerable industrial importance. The latter provides a synthetic entree to trimethylpyruvate and then tert-leucine, a building block of several peptidomimetric drugs and chiral catalysts. Stinson, S. E. *Chem. Eng. News* online at http://www.pubs.acs.org/hotartcl/cenear/960715/page.html. Though existing procedures use $H_2SO_4$ or $H_3PO_4$ to catalyze the reaction, interest has been expressed in the replacement of these species by solid acids. Using various solid acid catalysts, reported yields of pinacolone range from 2%–71%, but long reaction periods are typical, and the use of a volatile organic solvent is required, complicating isolation. Hsien, M.; Sheu, H.-T.; Lee, T.; Cheng, S. and Lee, J.-F. *J. Mol. Cat. A: Chemical* 2002, 181, 189–200. Using 2a as catalyst/solvent, we obtained an unoptimized yield of pinacolone of 35% during a one-hour reaction period, and an 88% yield of benzopinacolone over a two-hour period. Moreover, the pinacolone is readily distilled as a pure compound straight from the reaction milieu, unreacted pinacol being retained by the solvent/catalyst phase.

Ultimately, the ease with which these IL are recycled is central to their utility. Consequently, we examined the formation of ethyl acetate, an important commodity ester, from ethanol and acetic acid using 2a as the solvent/catalyst in a batch-type process, i.e., recycling the 2a. Otera, J. Angew. Chem. Int. Ed. 2001, 40, 2044–2045. The results of a representative round of recycling experiments are summarized below in Table 1.

TABLE 1

Recycling of 2a in the synthesis of ethyl acetate.

| Cycle | Ethyl acetate, %[a] |
|---|---|
| 1 | 82 |
| 2 | 91 |
| 3 | 96 |
| 4 | 81 |
| 5[b] | 87 |

[a]isolated yield.
[b]using regenerated 2a plus water.

As shown, the yield of the ester increases from cycles 1 to 3, only to drop off again in cycle 4. During these cycles, the mass of the solvent/catalyst medium also increases, consistent with the entrapment of materials by the cooled catalyst phase. Post-cycling analysis of the IL by GC and NMR was consistent with the retention of appreciable quantities of water and acetic acid. When heated under vacuum to remove these volatile materials, the catalytic activity of 2a was found to increase, in line with the degree to which water is removed from the system.

For an equilibrium reaction in which water is a product, the initial increase in ester yield accompanying the retention of water in cycles 1–3 was unexpected. It appears that for reasons yet to be determined, the presence of a threshold quantity of water in the ionic liquid contributes to higher reaction yields. To test the plausibility of this theory, we charged a dried sample of 2a with a bolus of water, estimated to be equivalent to the cumulative amount retained after cycles 1 abd 2; we found the yield (entry 5) of ethyl acetate to be greater than that obtained using dried 2a (entry 1).

Overall, the IL are versatile solvent/catalysts for the reactions examined, and provide further examples of the capacity of ionic liquids to be fashioned for specific chemical applications. They provide good product selectivities as well as a balance between the yields achievable using a homogeneous acid catalyst and the ease of catalyst/substrate separation provided by a heterogeneous catalyst.

Carbon Dioxide Capture by a Task-Specific Ionic Liquid

Remarkably, we have discovered an IL that captures $CO_2$. The cation of this new task-specific ionic liquid consists of an imidazolium ion to which a primary amine moiety is covalently tethered. This salt readily and reversibly sequesters $CO_2$. The ionic liquid is prepared from commercially available starting materials. The cation core is assembled by the reaction of 1-butylimidazole with 2-bromopropylamine hydrobromide in ethanol. After 24 h under reflux, the ethanol is removed in vacuo and the solid residue dissolved in a minimal quantity of water which is brought to ~pH 8 by the addition, in small portions, of solid KOH. The product imidazolium bromide is then separated from the KBr by-product by evaporation of the water, followed by extraction of the residue with ethanol-THF, in which the imidazolium salt is soluble. Subsequent ion exchange using $NaBF_4$ in ethanol/water gave the product salt 1 in 58% overall yield. NMR and FAB-MS verify the structure and composition of the IL. After drying under vacuum at 80° C., the product is a relatively viscous, water-free liquid that may be used directly for $CO_2$ sequestration. See Scheme 2.

Scheme 2. Proposed reaction between TSIL 1 and $CO_2$.

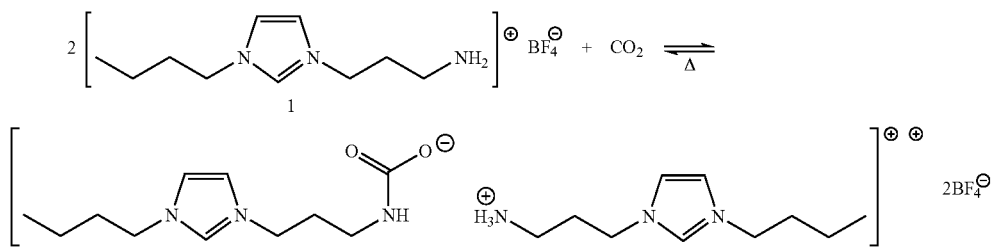

Consistent with observations by Brennecke and co-workers, $CO_2$ at 1 atm exhibits intrinsic solubility in the "conventional" ionic liquid phase 1-hexyl-3-methyl imidazolium hexafluorophosphate, [6-mim]$PF_6$. Blanchard, L. A. et al. Nature 1999, 399, 28–31; and Blanchard, L. A. et al. J. Phys. Chem. B 2001, 105, 2437. This is manifested by a 0.0881% increase in mass of the IL upon exposure to $CO_2$, and also by the FT-IR spectrum of the gas-treated IL, which has peaks characteristic of dissolved $CO_2$ at 2380 and 2400 cm.$^{-1}$ In a similar fashion, 1 exhibits a mass increase when exposed to $CO_2$, but one that considerably exceeds that observed with [6-mim]$PF_6$. When 1.2896 g of pure 1 is exposed to a stream of dry $CO_2$ for 3 h at 1 atm at room temperature (~295 K), a total mass gain of 0.0948 g (7.4%) is observed, a vastly greater increase than that observed for [6-mim]$PF_6$.

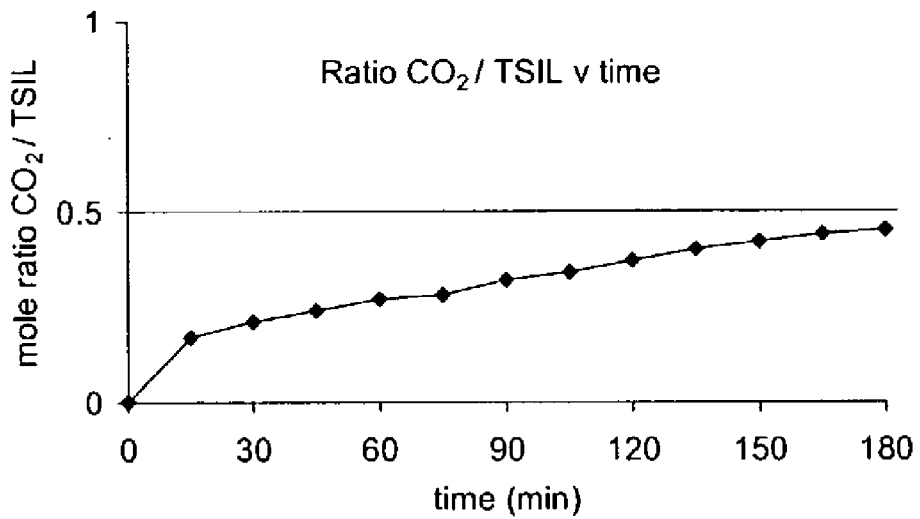
CO₂/TSIL molar ratio as a function of time.

$CO_2$/TSIL Molar Ratio as a Function of Time

The molar uptake of $CO_2$ per mole of TSIL during the 3 h exposure period approaches 0.5, the theoretical maximum for $CO_2$ sequestration as an ammonium carbamate salt. This per mole uptake of $CO_2$ by the amine-appended TSIL is comparable to those of standard sequestering amines, such as monoethanolamine (MEA), $\beta,\beta'$-hydroxyaminoethylether (DGA) and diisopropanolamine (DIPA). The process of $CO_2$ uptake is reversible; $CO_2$ extruded from the IL upon heating (80°–100° C.) for several hours under vacuum. The recovered ionic liquid has been recycled (five cycles) for $CO_2$ uptake with no observed loss of efficiency.

Significantly, the sequestration of $CO_2$ by the TSIL is borne out by comparison of the FT-IR and NMR spectra of the gas-untreated and gas-treated materials. In the FT-IR, the spectrum of the $CO_2$ treated material manifests a new absorption at 1666 $cm^{-1}$, consistent with a carbamate C=O stretch. Among the other prominent IR changes are those associated with N—H resonances. Centered at 3238 $cm^{-1}$, a broad amide N—H band with considerable fine structure is now present. Another broad new band is centered around 3623 $cm^{-1}$, and is assigned as an ammonium N—H stretch. Equally noteworthy is the virtual absence of bands associated with dissolved $CO_2$. When subjected to heating under vacuum, the FT-IR spectrum of the sample returns to a pre-$CO_2$ exposure appearance.

The $^{13}C$-NMR spectrum of the $CO_2$ treated product also supportsformation of a TSIL-ammonium carbamate. Most notably, a new resonance is observed at $\delta$ 158.11, attributable to a carbamate carbonyl carbon. Also new is a peak at 56.52 ppm, consistent with a methylene carbon attached to the carbamate nitrogen atom. The other features of the spectrum generally consist of peaks near those of the starting free-amine TSIL. However, the new resonances are "doubled" due to one-half of the amine TSIL becoming each a carbamate- and an ammonium-appended species.

Various Applications of Ionic Liquids

Ionic liquids that preferentially dissolve certain gaseous species can be used in conventional gas absorption applications. The non-volatile nature of ionic liquids plays two important roles. First, there will be no cross-contamination of the gas stream by the solvent during operation. This means no solvent loss and no air pollution. Second, regeneration of the solvent is easy; a simple flash or mild distillation step is all that is required to remove the gas from the solvent, again with no cross-contamination.

In addition to their use as conventional absorbents, ionic liquids may be immobilized on a support and used in a supported liquid membrane (SLM). The membrane will work if a gas preferentially dissolves in the liquid. SLMs may be used in a continuous separation process without a regeneration step. Conventional SLM technology is undermined by the fact that the liquid in which the gas dissolves eventually evaporates, thus rendering the membrane useless. Since ionic liquids are completely non-volatile, this problem is eliminated.

Ionic liquids also find use in the conversion of brown coal and oil shale into value-added products, such as alternative synthetic fuels and/or high-quality chemical feedstocks. For example, 1-butyl-3-methyl imidazolium, has been used to extract organic compounds from Estonian oil shale kerogen at various temperatures. Results at 175° C. yielded soluble products with an increase of ten times over that obtained using conventional organic solvents.

Bronsted-acidic ILs also act as proton shuttles, functionally carrying protons from acidic resin surfaces (e.g., Nafion) to the surrounding medium, where they are more free to react than if the proton is held at the polymer surface. Moreover, the Bronsted-acidic ILs have absolutely no vapor pressure when dissolved in water. For example, a relatively concentrated solution of HCl gives off HCl gas; in contrast, a Bronsted-acidic IL gives off no gaseous acid—pH paper suspended above the surface does not change colors!

Many product streams, particularly in the field of petroleum chemistry, include olefins and non-olefins. For example, ethane crackers tend to produce a mixture of ethane and ethylene. The ethylene is typically separated from the ethane via distillation. Because the boiling points of ethylene and ethane are relatively close to one another, the distillation is typically done at very low temperatures and/or high pressures; the separation is relatively expensive. The same problems are observed when separating propane from propylene in dehydrogenation facilities. Ionic liquids are useful is separating such mixtures. For example, an ionic liquid with a pendant functional group that coordinates the pi-bond of an olefin may be used to dissolve selectively the olefinic components of such a mixture. Likewise, an ionic liquid with a pendant functional group that coordinates a transition metal capable of coordinating the pi-bond of an olefin may be used to dissolve selectively the olefinic components of such a mixture. In either case, the dissolved olefins subsequently can be isolated by desorption.

Definitions

For convenience, certain terms employed in the specification, examples, and appended claims are collected here.

The articles "a" and "an" are used herein to refer to one or to more than one (i.e. to at least one) of the grammatical object of the article. By way of example, "an element" means one element or more than one element.

The term "ionic liquid" as used herein means an organic salt or hydrate thereof with a melting point less than about 150 C.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, ineta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

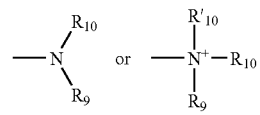

wherein $R_9$, $R_{10}$ and $R'_{10}$ each independently represent a group permitted by the rules of valence.

The term "acylamino" is art-recognized and refers to a moiety that can be represented by the general formula:

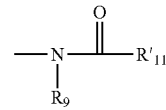

wherein $R_9$ is as defined above, and $R'_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

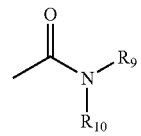

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

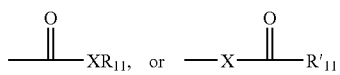

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

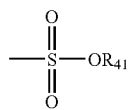

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The term "sulfate" is art recognized and includes a moiety that can be represented by the general formula:

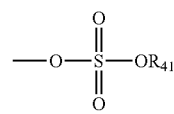

in which $R_{41}$ is as defined above.

The term "sulfonylamino" is art recognized and includes a moiety that can be represented by the general formula:

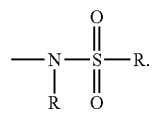

The term "sulfamoyl" is art-recognized and includes a moiety that can be represented by the general formula:

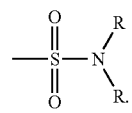

The term "sulfonyl", as used herein, refers to a moiety that can be represented by the general formula:

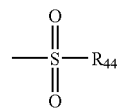

in which $R_{44}$ is selected from the group consisting of hydrogen, alkyl, alkenyl, alkynyl, cycloalkyl, heterocyclyl, aryl, or heteroaryl.

The term "silfoxido" as used herein, refers to a moiety that can be represented by the general formula:

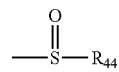

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. Moreover, the enantiomers of a racemic mixture may be separated using chiral chromatography, e.g., chiral HPLC.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

Compounds of the Invention

In certain embodiments, the present invention relates to a salt represented by 1:

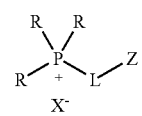

wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_n$, or (C(R$^3$)$_2$)$_n$AR(C(R$^3$)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a salt represented by 1 and the attendant definitions, wherein R represents independently for each occurrence aryl.

In certain embodiments, the present invention relates to a salt represented by 1 and the attendant definitions, wherein Z represents —SO$_3$H or —N(R')$_2$.

In certain embodiments, the present invention relates to a salt represented by 1 and the attendant definitions, wherein L represents (C(R$^3$)$_2$)$_n$.

In certain embodiments, the present invention relates to a salt represented by 1 and the attendant definitions, wherein X$^-$ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 1 and the attendant definitions, wherein X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 1 and the attendant definitions, wherein X$^-$ represents bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 1 and the attendant definitions, wherein X$^-$ represents bis(trifluoromethanesulfonyl)amide or (trifluoromethanesulfonyl)(trifluoroacetyl)amide.

In certain embodiments, the present invention relates to a salt represented by 1 and the attendant definitions, wherein R represents independently for each occurrence aryl; and Z represents —SO$_3$H or —N(R')$_2$.

In certain embodiments, the present invention relates to a salt represented by 1 and the attendant definitions, wherein R represents independently for each occurrence aryl; Z represents —SO$_3$H or —N(R')$_2$; and L represents (C(R$^3$)$_2$)$_n$.

In certain embodiments, the present invention relates to a salt represented by 1 and the attendant definitions, wherein R represents independently for each occurrence aryl; Z represents —SO$_3$H or —N(R')$_2$; L represents (C(R$^3$)$_2$)$_n$; and X$^-$ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 1 and the attendant definitions, wherein R represents independently for each occurrence aryl; Z represents —SO$_3$H or —N(R')$_2$; L represents (C(R$^3$)$_2$)$_n$; and X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 1 and the attendant definitions, wherein R represents independently for each occurrence aryl; Z represents —SO$_3$H or —N(R')$_2$; L represents (C(R$^3$)$_2$)$_n$; and X$^-$ represents bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 1 and the attendant definitions, wherein R represents independently for each occurrence aryl; Z represents —SO$_3$H or —N(R')$_2$; L represents (C(R$^3$)$_2$)$_n$; and X$^-$ represents bis(trifluoromethanesulfonyl)amide or (trifluoromethanesulfonyl)(trifluoroacetyl)amide.

In certain embodiments, the present invention relates to a salt represented by 2:

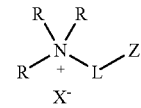

wherein

R represents independently for each occurrence alkyl, fluoroalkyl, cycloalkyl, aryl, heteroaryl, aralkyl, heteroaralkyl, or —(CH$_2$)$_n$—R$_8$; or $^+$NR$_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a salt represented by 2 and the attendant definitions, wherein R represents independently for each occurrence alkyl or aryl.

In certain embodiments, the present invention relates to a salt represented by 2 and the attendant definitions, wherein Z represents —SO$_3$H or —N(R')$_2$.

In certain embodiments, the present invention relates to a salt represented by 2 and the attendant definitions, wherein L represents (C(R$^3$)$_2$)$_n$.

In certain embodiments, the present invention relates to a salt represented by 2 and the attendant definitions, wherein X⁻ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 2 and the attendant definitions, wherein X⁻ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 2 and the attendant definitions, wherein X⁻ represents bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 2 and the attendant definitions, wherein X⁻ represents bis(trifluoromethanesulfonyl)amide or (trifluoromethanesulfonyl)(trifluoroacetyl)amide.

In certain embodiments, the present invention relates to a salt represented by 2 and the attendant definitions, wherein R represents independently for each occurrence alkyl or aryl; and Z represents —SO₃H or —N(R')₂.

In certain embodiments, the present invention relates to a salt represented by 2 and the attendant definitions, wherein R represents independently for each occurrence alkyl or aryl; Z represents —SO₃H or —N(R')₂; and L represents (C(R³)₂)ₙ.

In certain embodiments, the present invention relates to a salt represented by 2 and the attendant definitions, wherein R represents independently for each occurrence alkyl or aryl; Z represents —SO₃H or —N(R')₂; L represents (C(R³)₂)ₙ; and X⁻ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 2 and the attendant definitions, wherein R represents independently for each occurrence alkyl or aryl; Z represents —SO₃H or —N(R')₂; L represents (C(R³)₂)ₙ; and X⁻ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 2 and the attendant definitions, wherein R represents independently for each occurrence alkyl or aryl; Z represents —SO₃H or —N(R')₂; L represents (C(R³)₂)ₙ; and X⁻ represents bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 2 and the attendant definitions, wherein R represents independently for each occurrence alkyl or aryl; Z represents —SO₃H or —N(R')₂; L represents (C(R³)₂)ₙ; and X⁻ represents bis(trifluoromethanesulfonyl)amide or (trifluoromethanesulfonyl)(trifluoroacetyl)amide.

In certain embodiments, the present invention relates to a salt represented by 3:

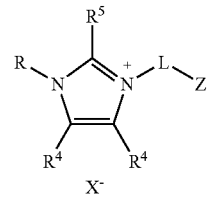

3 wherein

R represents independently for each occurrence alkyl, fluoroalkyl, cycloalkyl, aryl, heteroaryl, aralkyl, heteroaralkyl, or —(CH₂)ₙ—R₈;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH₂)ₙ—R₈;

R" represents independently for each occurrence H, alkyl, fluoroalkyl, aryl, heteroaryl, aralkyl, heteroaralkyl, or —(CH₂)ₙ—R₈;

R³ represents independently for each occurrence H, F, or alkyl;

R⁴ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH₂)ₙ—R₈;

R⁵ represents independently for each occurrence H, alkyl, fluoroalkyl, aryl, heteroaryl, aralkyl, heteroaralkyl, or —(CH₂)ₙ—R₈;

L represents (C(R³)₂)ₙ, (C(R³)₂)ₙJ(C(R³)₂)ₘ, or (C(R³)₂)ₙAR(C(R³)₂)ₘ;

Z represents —SO₃H, —CO₂H, —CO₂R, —C(O)N(R")₂, —C(O)N(R")N(R")₂, —N(R')₂, —OR', —SR', —S(O)R", —S(O)₂R", —CN, —N(R")P(O)(R)₂, —C(OR')(R")₂, alkenyl, or alkynyl;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R₈ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to a salt represented by 3 and the attendant definitions, wherein R represents independently for each occurrence alkyl.

In certain embodiments, the present invention relates to a salt represented by 3 and the attendant definitions, wherein R⁴ represents independently for each occurrence H or alkyl.

In certain embodiments, the present invention relates to a salt represented by 3 and the attendant definitions, wherein R⁵ represents independently for each occurrence H or alkyl.

In certain embodiments, the present invention relates to a salt represented by 3 and the attendant definitions, wherein $R^5$ represents independently for each occurrence alkyl.

In certain embodiments, the present invention relates to a salt represented by 3 and the attendant definitions, wherein Z represents —SO$_3$H or —N(R')$_2$.

In certain embodiments, the present invention relates to a salt represented by 3 and the attendant definitions, wherein L represents (C(R$^3$)$_2$)$_n$.

In certain embodiments, the present invention relates to a salt represented by 3 and the attendant definitions, wherein X$^-$ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 3 and the attendant definitions, wherein X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 3 and the attendant definitions, wherein X$^-$ represents bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 3 and the attendant definitions, wherein X$^-$ represents bis(trifluoromethanesulfonyl)amide or (trifluoromethanesulfonyl)(trifluoroacetyl)amide.

In certain embodiments, the present invention relates to a salt represented by 3 and the attendant definitions, wherein R represents independently for each occurrence alkyl; and Z represents —SO$_3$H or —N(R')$_2$.

In certain embodiments, the present invention relates to a salt represented by 3 and the attendant definitions, wherein R represents independently for each occurrence alkyl; Z represents —SO$_3$H or —N(R')$_2$; and L represents (C(R$^3$)$_2$)$_n$.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; and X$^-$ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; and X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; and X$^-$ represents bis(methanesulfonyl)amide, bis(trifluoromethanesulfonyl)amide, bis(benzenesulfonyl)amide, or bis(p-toluenesulfonyl)amide.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; and X$^-$ represents bis(trifluoromethanesulfonyl)amide or (trifluoromethanesulfonyl)(trifluoroacetyl)amide.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; X$^-$ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; and R$^4$ represents independently for each occurrence H or alkyl.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; and R$^4$ represents independently for each occurrence H or alkyl.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; X$^-$ represents bis(methanesulfonyl)amide, bis(trifluoromethanesulfonyl)amide, bis(benzenesulfonyl)amide, or bis(p-toluenesulfonyl)amide; and R$^4$ represents independently for each occurrence H or alkyl.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; X$^-$ represents bis(trifluoromethanesulfonyl)amide; and R$^4$ represents independently for each occurrence H or alkyl.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; X$^-$ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; R$^4$ represents independently for each occurrence H or alkyl; and R$^5$ represents independently for each occurrence H or alkyl.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; R$^4$ represents independently for each occurrence H or alkyl; and R$^5$ represents independently for each occurrence H or alkyl.

In certain embodiments, the present invention relates to a salt represented by 3 and the attendant definitions, wherein R represents independently for each occurrence alkyl; Z represents —SO$_3$H or —N(R')$_2$; L represents (C(R$^3$)$_2$)$_n$; X$^-$ represents bis(methanesulfonyl)amide, bis(trifluoromethanesulfonyl)amide, bis(benzenesulfonyl)amide, or bis(p-toluenesulfonyl)amide; R$^4$ represents independently for each occurrence H or alkyl; and R$^5$ represents independently for each occurrence H or alkyl.

In certain embodiments, the present invention relates to a salt represented by 3 and the attendant definitions, wherein R represents independently for each occurrence alkyl; Z represents —$SO_3H$ or —$N(R')_2$; L represents $(C(R^3)_2)_n$; $X^-$ represents bis(trifluoromethanesulfonyl)amide; $R^4$ represents independently for each occurrence H or alkyl; and $R^5$ represents independently for each occurrence H or alkyl.

In certain embodiments, the present invention relates to a salt represented by 3 and the attendant definitions, wherein R represents independently for each occurrence alkyl; Z represents —$SO_3H$ or —$N(R')_2$; L represents $(C(R^3)_2)_n$; $X^-$ represents boron tetrafluoride, phosphorus hexafluoride, methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; $R^4$ represents independently for each occurrence H or alkyl; and $R^5$ represents independently for each occurrence alkyl.

In certain embodiments, the present invention relates to a salt represented by 3 and the attendant definitions, wherein R represents independently for each occurrence alkyl; Z represents —$SO_3H$ or —$N(R')_2$; L represents $(C(R^3)_2)_n$; $X^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; $R^4$ represents independently for each occurrence H or alkyl; and $R^5$ represents independently for each occurrence alkyl.

In certain embodiments, the present invention relates to a salt represented by 3 and the attendant definitions, wherein R represents independently for each occurrence alkyl; Z represents —$SO_3H$ or —$N(R')_2$; L represents $(C(R^3)_2)_n$; $X^-$ represents bis(methanesulfonyl)amide, bis(trifluoromethanesulfonyl)amide, bis(benzenesulfonyl)amide, or bis(p-toluenesulfonyl)amide; $R^4$ represents independently for each occurrence H or alkyl; and $R^5$ represents independently for each occurrence alkyl.

In certain embodiments, the present invention relates to a salt represented by 3 and the attendant definitions, wherein R represents independently for each occurrence alkyl; Z represents —$SO_3H$ or —$N(R')_2$; L represents $(C(R^3)_2)_n$; $X^-$ represents bis(trifluoromethanesulfonyl)amide; $R^4$ represents independently for each occurrence H or alkyl; and $R^5$ represents independently for each occurrence alkyl.

Methods of the Invention

In certain embodiments, the present invention relates to the use of an IL with an appended amine (e.g., primary, secondary, tertiary, or heterocyclic) for the capture from the gas phase of an acidic gas, including but not limited to $H_2S$, $CO_2$, COS, $SO_2$, and $SO_3$.

In certain embodiments, the present invention relates to the use of an IL with an appended amine (e.g., primary, secondary, tertiary, or heterocyclic) in conjunction with water for the capture of an acidic gas from the gas phase.

In certain embodiments, the present invention relates to the use of an IL with an appended amine (e.g., primary, secondary, tertiary, or heterocyclic) dissolved in a molecular solvent or other ionic liquid for the capture of an acidic gas from the gas phase.

In certain embodiments, the present invention relates to the use of an IL with an appended amine dissolved in water or other solvent as a non-odorous, non-volatile base for a general-base-catalyzed reaction.

In certain embodiments, the present invention relates to the use of an IL with an appended amine as a scavaging agent for an amine-reactive material in the solution phase.

In certain embodiments, the present invention relates to the use of an IL with an appended amine as a solvent.

In certain embodiments, the present invention relates to the use of an IL with an appended amine (e.g., primary, secondary, tertiary or heterocyclic) alone or in conjunction with an organic molecule, such as salicylaldehyde, for the extraction of a metal ion from an aqueous solution.

In certain embodiments, the present invention relates to the use of an IL with an appended amine in conjunction with an ion-exchange resin, clay or zeolite for any of the aforementioned applications.

In certain embodiments, the present invention relates to the use of an IL with an appended acidic group for general or specific acid catalysis, either as a pure material, or as a solution in another ionic liquid or molecular solvent. Such reactions include, but are not limited to, Fischer esterification, pinnacol rearrangement, alcohol dehydration, rearrangements, isomerizations, Friedel-Crafts alkylation and acylation, or aromatic nitration.

In certain embodiments, the present invention relates to the use of an IL with an appended acidic group as a scavaging agent for an acid-reactive material in the gas or solution phase.

In certain embodiments, the present invention relates to the use of an IL with an appended acidic group as a dehydrating or drying agent.

In certain embodiments, the present invention relates to the use of an IL with an appended acid in conjunction with an ion-exchange resin, clay or zeolite for any of the aforementioned applications.

In certain embodiments, the present invention relates to the use of an IL with an appended acidic group as a solvent.

In certain embodiments, the present invention relates to the use of an IL with an appended fluoroketone or fluoroalcohol group as a solvent; as an acid; or as an activator of peroxide for use in an oxidation reaction.

In certain embodiments, the present invention relates to the use of an IL with an appended sulfone, sulfoxide or sulfonamide group in a liquid-liquid or liquid-gas separation, including a separation in the refining of petroleum or petrochemicals.

In certain embodiments, the present invention relates to the use of an IL with an appended sulfone, sulfoxide or sulfonamide group as a solvent for a polar molecule, including but not limited to biomolecules, such as saccharides, amino acids, nucleic acids, proteins, enzymes, DNA and RNA.

In certain embodiments, the present invention relates to the use of an IL with an appended sulfone, sulfoxide or sulfonamide group as a solvent.

In certain embodiments, the present invention relates to the use of an IL with an appended sulfone, sulfoxide or sulfonamide group as a phase-transfer adjuvant for use in conjunction with a supercritical solvent, e.g., supercritical $CO_2$.

In certain embodiments, the present invention relates to the use of an IL with an appended sulfonyl halide group as a scavaging reagent for use in conjunction with a reactive species.

In certain embodiments, the present invention relates to the use of an IL with an appended sulfone or sulfoxide group in conjunction with ion exchangeable materials, such as ion exchange resins, clays, and zeolites, for any of the aforementioned uses.

In certain embodiments, the present invention relates to the use of an IL with an appended amide, urea or thiourea group in a liquid-liquid or liquid-gas separation, including separations in the refining of petroleum or petrochemicals.

In certain embodiments, the present invention relates to the use of an IL with an appended amide, urea or thiourea group as a solvent for a polar molecule, including but not limited to biomolecules, such as saccharides, amino acids, nucleic acids, proteins, enzymes, DNA and RNA.

In certain embodiments, the present invention relates to the use of an IL with an appended amide, urea or thiourea group as a solvent.

In certain embodiments, the present invention relates to the use of an IL with an appended amide, urea or thiourea group in conjunction with an ion exchangeable material, such as ion exchange resins, clays, and zeolites, for any of the aforementioned uses.

In certain embodiments, the present invention relates to the use of an IL with an appended amide, urea or thiourea group as a phase-transfer adjuvant for use in conjunction with a supercritical solvent, e.g., supercritical $CO_2$.

In certain embodiments, the present invention relates to the use of a phosphoramide appended IL, alone or in conjunction with another ionic liquid or a molecular solvent, as a solvent or for the extraction of a metal from an ore or immiscible solution phase.

In certain embodiments, the present invention relates to the use of a functionalized IL as a solvent, reagent-solvent, or a catalyst-solvent for a polymerization or a polymer-processing operation.

In certain embodiments, the present invention relates to the use of a functionalized IL as an anti-static agent, e.g., in a solution, petroleum or a petrochemical.

In certain embodiments, the present invention relates to a method of removing carbon dioxide, carbonyl sulfide, sulfur dioxide, sulfur trioxide, hydrogen sulfide or a carbonyl-containing compound from a gaseous or liquid mixture, comprising the step of exposing a gaseous or liquid mixture to a salt selected from the group consisting of:

salts represented by 1:

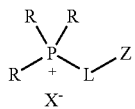

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

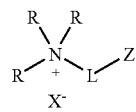

wherein

R represents independently for each occurrence alkyl, fluoroalkyl, cycloalkyl, aryl, heteroaryl, aralkyl, heteroaralkyl, or —$(CH_2)_n$—$R_8$; or $^+NR_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

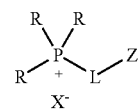

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_m$—$R_8$;

$R^3$ represents independently for each occurrence H, F, or alkyl;

$R^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

$R^5$ represents independently for each occurrence H, alkyl, fluoroalkyl, aryl, heteroaryl, aralkyl, heteroaralkyl, or —$(CH_2)_n$—$R_8$;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to the aforementioned method and the attendant definitions, wherein Z represents independently for each occurrence —$N(R')_2$.

In certain embodiments, the present invention relates to the aforementioned method and the attendant definitions, wherein said gaseous or liquid mixture is natural gas.

In certain embodiments, the present invention relates to the aforementioned method and the attendant definitions, wherein carbon dioxide is removed.

In certain embodiments, the present invention relates to the aforementioned method and the attendant definitions, wherein the salt is dissolved in water.

In certain embodiments, the present invention relates to the aforementioned method and the attendant definitions, wherein Z represents independently for each occurrence —$N(R')_2$; and said gaseous or liquid mixture is natural gas.

In certain embodiments, the present invention relates to a method of transporting carbon dioxide, carbonyl sulfide, sulfur dioxide, sulfur trioxide, hydrogen sulfide or a carbonyl-containing compound from a first gaseous or liquid mixture to a second gaseous or liquid mixture, comprising the step of exposing a first gaseous or liquid mixture to a salt selected from the group consisting of:

salts represented by 1:

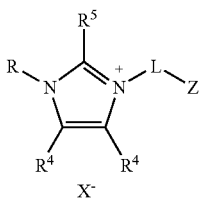

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$, —$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$N(R')_2$, —OR', —SR', or —$C(OR')(R")_2$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

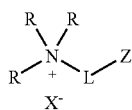

wherein

R represents independently for each occurrence alkyl, fluoroalkyl, cycloalkyl, aryl, heteroaryl, aralkyl, heteroaralkyl, or —(CH$_2$)$_n$—R$_8$; or $^+$NR$_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_m$, (C(R$^3$)$_2$)$_n$J(C(R$^3$)$_2$)$_m$, or (C(R$^3$)$_2$)$_n$AR(C(R$^3$)$_2$)$_m$;

Z represents —N(R')$_2$, —OR', —SR', or —C(OR')(R")$_2$;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

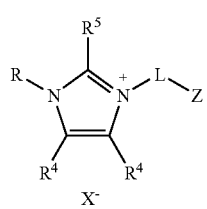

wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

R$^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R$^5$ represents independently for each occurrence H, alkyl, fluoroalkyl, aryl, heteroaryl, aralkyl, heteroaralkyl, or —(CH$_2$)$_n$—R$_8$;

L represents (C(R$^3$)$_2$)$_m$, (C(R$^3$)$_2$)$_n$J(C(R$^3$)$_2$)$_m$, or (C(R$^3$)$_2$)$_n$AR(C(R$^3$)$_2$)$_m$;

Z represents —N(R')$_2$, —OR', —SR', or —C(OR')(R")$_2$;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and exposing subsequently said salt to a second gaseous or liquid mixture, thereby transporting carbon dioxide, carbonyl sulfide, sulfur dioxide, sulfur trioxide, hydrogen sulfide or a carbonyl-containing compound to said second gaseous or liquid mixture.

In certain embodiments, the present invention relates to the aforementioned method and the attendant definitions, wherein Z represents independently for each occurrence —N(R')$_2$.

In certain embodiments, the present invention relates to the aforementioned method and the attendant definitions, wherein said salt is contained within a semi-permeable membrane.

In certain embodiments, the present invention relates to the aforementioned method and the attendant definitions, wherein Z represents independently for each occurrence —N(R')$_2$; and said salt is contained within a semi-permeable membrane.

In certain embodiments, the present invention relates to a method of removing an alkene, alkyne or carbon monoxide from a mixture, comprising the step of exposing a mixture to a complex formed from a transition metal and a salt selected from the group consisting of:

salts represented by 1:

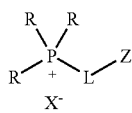

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$SO_3H$, —$CO_2H$, —$CO_2R$, —$C(O)N(R")_2$, —$C(O)N(R")N(R")_2$, —$N(R')_2$, —OR', —SR', —S(O)R", —$S(O)_2R"$, —CN, —$N(R")P(O)(R)_2$, —$C(OR')(R")_2$, alkenyl, or alkynyl;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

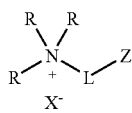

wherein

R represents independently for each occurrence alkyl, fluoroalkyl, cycloalkyl, aryl, heteroaryl, aralkyl, heteroaralkyl, or —$(CH_2)_n$—$R_8$; or $^+NR_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R_3$ represents independently for each occurrence H, F, or alkyl;

L represents $(C(R^3)_2)_n$, $(C(R^3)_2)_n J(C(R^3)_2)_m$, or $(C(R^3)_2)_n AR(C(R^3)_2)_m$;

Z represents —$SO_3H$, —$CO_2H$, —$CO_2R$, —$C(O)N(R")_2$, —$C(O)N(R")N(R")_2$, —$N(R')_2$, —OR', —SR', —S(O)R", —$S(O)_2R"$, —CN, —$N(R")P(O)(R)_2$, —$C(OR')(R")_2$, alkenyl, or alkynyl;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

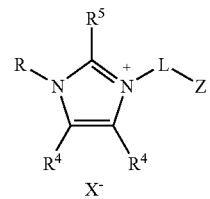

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

$R^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R$^5$ represents independently for each occurrence H, alkyl, fluoroalkyl, aryl, heteroaryl, aralkyl, heteroaralkyl, or —(CH$_2$)$_n$—R$_8$;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to the aforementioned method and the attendant definitions, wherein Z represents independently for each occurrence alkenyl or alkynyl; and the transition metal is selected from groups 8–11 of the Periodic Table.

In certain embodiments, the present invention relates to the aforementioned method and the attendant definitions, wherein Z represents independently for each occurrence alkenyl or alkynyl; and the transition metal is iron, cobalt, nickel, copper, ruthenium, rhodium, palladium, silver, iridium or platinum.

In certain embodiments, the present invention relates to the aforementioned method and the attendant definitions, wherein Z represents independently for each occurrence alkenyl or alkynyl; and the transition metal is silver.

In certain embodiments, the present invention relates to a method of catalyzing an acid-catalyzed chemical reaction to give a product, comprising the step of exposing a reactant mixture to a salt selected from the group consisting of:

salts represented by 1:

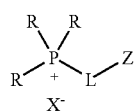

wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H or —CO$_2$H;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

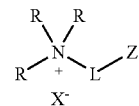

wherein

R represents independently for each occurrence alkyl, fluoroalkyl, cycloalkyl, aryl, heteroaryl, aralkyl, heteroaralkyl, or —(CH$_2$)$_n$—R$_8$; or $^+$NR$_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H or —CO$_2$H;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

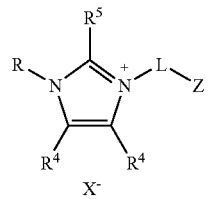

wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

$R^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

$R^5$ represents independently for each occurrence H, alkyl, fluoroalkyl, aryl, heteroaryl, aralkyl, heteroaralkyl, or —$(CH_2)_n$—$R_8$;

L represents $(C(R^3)_2)_n$, $(C(R^3)_2)_n J(C(R^3)_2)_m$, or $(C(R^3)_2)_n AR(C(R^3)_2)_m$;

Z represents —$SO_3H$ or —$CO_2H$;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to the aforementioned method and the attendant definitions, wherein Z represents independently for each occurrence —$SO_3H$.

In certain embodiments, the present invention relates to the aforementioned method and the attendant definitions, wherein said reactant mixture comprises an alcohol; and said product is an ether.

In certain embodiments, the present invention relates to the aforementioned method and the attendant definitions, wherein said reactant mixture comprises an alcohol and a carboxylic acid; and said product is an ester.

In certain embodiments, the present invention relates to the aforementioned method and the attendant definitions, wherein said reactant mixture comprises an ester and water; and said product is a carboxylic acid.

In certain embodiments, the present invention relates to the aforementioned method and the attendant definitions, wherein said reactant mixture comprises an alcohol and a first ester; and said product is a second ester.

In certain embodiments, the present invention relates to the aforementioned method and the attendant definitions, wherein said reactant mixture comprises a 1,2-diol; and said product is a ketone.

In certain embodiments, the present invention relates to the aforementioned method and the attendant definitions, wherein said reactant mixture comprises an alcohol; and said product is an alkene.

In certain embodiments, the present invention relates to the aforementioned method and the attendant definitions, wherein said reactant mixture comprises a first alkene; and said product is a second alkene.

In certain embodiments, the present invention relates to the aforementioned method and the attendant definitions, wherein said reactant mixture comprises a first aromatic compound and a nitrating agent; and said product is a second aromatic compound comprising a nitro group.

In certain embodiments, the present invention relates to the aforementioned method and the attendant definitions, wherein said reactant mixture comprises a first aromatic compound and an alcohol; and said product is a second aromatic compound comprising an alkyl group.

In certain embodiments, the present invention relates to the aforementioned method and the attendant definitions, wherein said reactant mixture comprises a first aromatic compound and a carboxylic acid; and said product is a second aromatic compound comprising an acyl group.

In certain embodiments, the present invention relates to the aforementioned method and the attendant definitions, wherein Z represents independently for each occurrence —$SO_3H$; and said reactant mixture comprises an alcohol; and said product is an ether.

In certain embodiments, the present invention relates to the aforementioned method and the attendant definitions, wherein Z represents independently for each occurrence —$SO_3H$; and said reactant mixture comprises an alcohol and a carboxylic acid; and said product is an ester.

In certain embodiments, the present invention relates to the aforementioned method and the attendant definitions, wherein Z represents independently for each occurrence —$SO_3H$; and said reactant mixture comprises an ester and water; and said product is a carboxylic acid.

In certain embodiments, the present invention relates to the aforementioned method and the attendant definitions, wherein Z represents independently for each occurrence —SO₃H; and said reactant mixture comprises an alcohol and a first ester; and said product is a second ester.

In certain embodiments, the present invention relates to the aforementioned method and the attendant definitions, wherein Z represents independently for each occurrence —SO₃H; and said reactant mixture comprises a 1,2-diol; and said product is a ketone.

In certain embodiments, the present invention relates to the aforementioned method and the attendant definitions, wherein Z represents independently for each occurrence —SO₃H; said reactant mixture comprises an alcohol; and said product is an alkene.

In certain embodiments, the present invention relates to the aforementioned method and the attendant definitions, wherein Z represents independently for each occurrence —SO₃H; said reactant mixture comprises a first alkene; and said product is a second alkene.

In certain embodiments, the present invention relates to the aforementioned method and the attendant definitions, wherein Z represents independently for each occurrence —SO₃H; said reactant mixture comprises a first aromatic compound and a nitrating agent; and said product is a second aromatic compound comprising a nitro group.

In certain embodiments, the present invention relates to the aforementioned method and the attendant definitions, wherein Z represents independently for each occurrence —SO₃H; said reactant mixture comprises a first aromatic compound and an alcohol; and said product is a second aromatic compound comprising an alkyl group.

In certain embodiments, the present invention relates to the aforementioned method and the attendant definitions, wherein Z represents independently for each occurrence —SO₃H; said reactant mixture comprises a first aromatic compound and a carboxylic acid; and said product is a second aromatic compound comprising an acyl group.

In certain embodiments, the present invention relates to a method of catalyzing a base-catalyzed chemical reaction to give a product, comprising the step of exposing a reactant mixture to a salt selected from the group consisting of:

salts represented by 1:

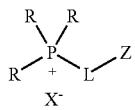

wherein

R represents independently for each occurrence alkyl, fluoroalkyl, cycloalkyl, aryl, heteroaryl, aralkyl, heteroaralkyl, or —(CH₂)ₙ—R₈;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH₂)ₙ—R₈;

R" represents independently for each occurrence H, alkyl, fluoroalkyl, aryl, heteroaryl, aralkyl, heteroaralkyl, or —(CH₂)ₙ—R₈;

R³ represents independently for each occurrence H, F, or alkyl;

L represents (C(R³)₂)ₙ, (C(R³)₂)ₙJ(C(R³)₂)ₘ, or (C(R³)₂)ₙ AR(C(R³)₂)ₘ;

Z represents —N(R')₂, —OR', —SR', or —C(OR')(R")₂;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R₈ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

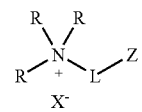

wherein

R represents independently for each occurrence alkyl, fluoroalkyl, cycloalkyl, aryl, heteroaryl, aralkyl, heteroaralkyl, or —(CH₂)ₙ, —R₈; or ⁺NR₃ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH₂)ₙ—R₈;

R" represents independently for each occurrence H, alkyl, fluoroalkyl, aryl, heteroaryl, aralkyl, heteroaralkyl, or —(CH₂)ₙ—R₈;

R³ represents independently for each occurrence H, F, or alkyl;

L represents (C(R³)₂)ₙ, (C(R³)₂)ₙJ(C(R³)₂)ₘ, or (C(R³)₂)ₙ AR(C(R³)₂)ₘ;

Z represents —N(R')₂, —OR', —SR', or —C(OR')(R")₂;

Ar represents independently for each occurrence aryl or heteroaryl;

J represents independently for each occurrence O, S, NR', cycloalkyl, or heterocyclyl;

X⁻ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R₈ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

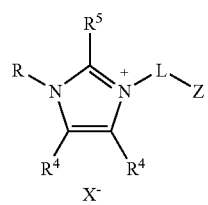

wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

R$^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R$^5$ represents independently for each occurrence H, alkyl, fluoroalkyl, aryl, heteroaryl, aralkyl, heteroaralkyl, or —(CH$_2$)$_n$—R$_8$;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —N(R')$_2$, —OR', —SR', or —C(OR')(R")$_2$;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

In certain embodiments, the present invention relates to the aforementioned method and the attendant definitions, wherein Z represents independently for each occurrence —N(R')$_2$.

In certain embodiments, the present invention relates to a method of preparing a solution, comprising the step of combining a solute and a solvent to produce a solution, wherein said solvent is selected from the group consisting of:

salts represented by 1:

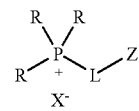

wherein

R represents independently for each occurrence alkyl, fluoroalkyl, cycloalkyl, aryl, heteroaryl, aralkyl, heteroaralkyl, or —(CH$_2$)$_n$—R$_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;

R" represents independently for each occurrence H, alkyl, fluoroalkyl, aryl, heteroaryl, aralkyl, heteroaralkyl, or —(CH$_2$)$_n$—R$_8$;

R$^3$ represents independently for each occurrence H, F, or alkyl;

L represents (C(R$^3$)$_2$)$_n$, (C(R$^3$)$_2$)$_n$J(C(R$^3$)$_2$)$_m$, or (C(R$^3$)$_2$)$_n$AR(C(R$^3$)$_2$)$_m$;

Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;

Ar represents independently for each occurrence aryl or heteroaryl;

J represents independently for each occurrence O, S, NR', cycloalkyl, or heterocyclyl;

X$^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

R$_8$ represents independently for each occurrence cycloalkyl, aryl, or heteroaryl;

m represents independently for each occurrence an integer in the range 1–10 inclusive; and n represents independently for each occurrence an integer in the range 1–10 inclusive;

salts represented by 2:

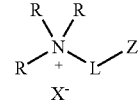

wherein

R represents independently for each occurrence alkyl, fluoroalkyl, cycloalkyl, aryl, heteroaryl, aralkyl, heteroaralkyl, or —(CH$_2$)$_n$—R$_8$; or $^+$NR$_3$ taken together represents pyridinium, imidazolium, benzimidazolium, pyrazolium, benzpyrazolium, indazolium, thiazolium, benzthiazolium, oxazolium, benzoxazolium, isoxazolium, isothiazolium, imdazolidenium, guanidinium, quinuclidinium, triazolium, tetrazolium, quinolinium, isoquinolinium, piperidinium, pyrrolidinium, morpholinium, pyridazinium, pyrazinium, piperazinium, triazinium, azepinium, or diazepinium;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

L represents $(C(R^3)_2)_m$, $(C(R^3)_2)_n J(C(R^3)_2)_m$, or $(C(R^3)_2)_n AR(C(R^3)_2)_m$;

Z represents —$SO_3H$, —$CO_2H$, —$CO_2R$, —$C(O)N(R")_2$, —$C(O)N(R")N(R")_2$, —$N(R')_2$, —OR', —SR', —$S(O)R"$, —$S(O)_2R"$, —CN, —$N(R")P(O)(R)_2$, —$C(OR')(R")_2$, alkenyl, or alkynyl;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive; and salts represented by 3:

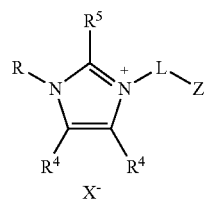

3 wherein

R represents independently for each occurrence alkyl, fluoroalkyl, cycloalkyl, aryl, heteroaryl, aralkyl, heteroaralkyl, or —$(CH_2)_n$—$R_8$;

R' represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

R" represents independently for each occurrence H, alkyl, fluoroalkyl, aryl, heteroaryl, aralkyl, heteroaralkyl, or —$(CH_2)_n$—$R_8$;

$R^3$ represents independently for each occurrence H, F, or alkyl;

$R^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —$(CH_2)_n$—$R_8$;

$R^5$ represents independently for each occurrence H, alkyl, fluoroalkyl, aryl, heteroaryl, aralkyl, heteroaralkyl, or —$(CH_2)_n$—$R_8$;

L represents $(C(R^3)_2)_m$, $(C(R^3)_2)_n J(C(R^3)_2)_m$, or $(C(R^3)_2)_n AR(C(R^3)_2)_m$;

Z represents —$SO_3H$, —$CO_2H$, —$CO_2R$, —$C(O)N(R")_2$, —$C(O)N(R")N(R")_2$, —$N(R')_2$, —OR', —SR', —$S(O)R"$, —$S(O)_2R"$, —CN, —$N(R")P(O)(R)_2$, —$C(OR')(R")_2$, alkenyl, or alkynyl;

Ar represents independently for each occurrence aryl or heteroaryl;

J represents independently for each occurrence O, S, NR', cycloalkyl, or heterocyclyl;

$X^-$ represents boron tetrafluoride, phosphorus tetrafluoride, phosphorus hexafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, halide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;

$R_8$ represents independently for each occurrence cycloalkyl, aryl, or heteroaryl;

m represents independently for each occurrence an integer in the range 1–10 inclusive; and n represents independently for each occurrence an integer in the range 1–10 inclusive.

Examplification

The invention now being generally described, it will be more readily understood by reference to the following examples, which are included merely for purposes of illustration of certain aspects and embodiments of the present invention, and are not intended to limit the invention.

EXAMPLE 1

Brønsted Acidic Ionic Liquids and their Use as Catalysts-Solvents

General Considerations $^1$H NMR (300 MHz) and $^{13}$C NMR (75 MHz) spectra were obtained as solutions in either $CDCl_3$ or $D_2O$. Chemical shifts were reported in parts per million (ppm, δ) and referenced to $CHCl_3$ (δ 7.27) or $D_2O$ (δ 4.88). Infrared spectra were recorded as a thin film on sodium chloride and absorptions were reported in wavenumbers ($cm^{-1}$). Melting points are uncorrected. Distillations were performed using a Kugelrohr ball-tube distillation apparatus. Gas chromatographic analyses were performed using an Agilent 6850 system (FID). TLC analyses were performed on Whatman flexible polyester backed TLC plates with a fluorescent indicator. Detection was conducted by UV absorption (254 nm) and charring with 10% $KMnO_4$ in water. Baker silica gel (47–61 microns) was used for all chromatographic separations. Anhydrous organic solvents were dried and then distilled prior to use. Acetic acid, acetic anhydride, benzopinacole, ethanol, hexanoic acid, 1-octanol, pinacol and p-toluenesulfonic acid were not purified prior to use. All other chemicals used for synthetic procedures were reagent grade or better. Solutions were concentrated in vacuo with a rotary evaporator and the residue was purified using a silica gel column unless specified otherwise.

Synthesis of triphenyl(propyl-3-sulphonyl)phosphonium toluenesulfonate

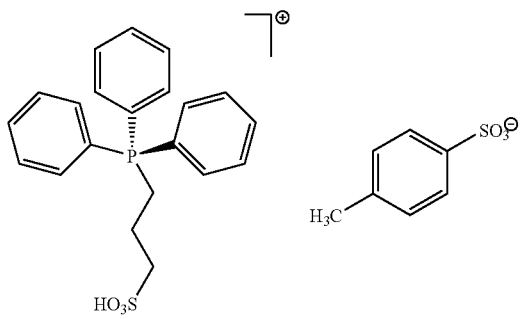

Triphenylphosphine and 1,3-propane sultone were combined in equimolar quantities in toluene and brought to reflux. Overnight, a white precipitate formed which was isolated by filtration and dried. Analysis of the solid revealed it to be the desired zwitterion, formed in quantitative yield. The desired zwitterion was of sufficient purity to be used without any further purification. Conversion to the ionic liquid was accomplished by combining equimolar quantities of pTSA hydrate and the zwitterion and heating to 70° C. for 24 h, during which time the solids liquefy, resulting in the formation of triphenyl(propyl-3-sulfonyl)phosphonium toluenesulfonate. The IL phase was then washed repeatedly with toluene and ether to remove non-ionic residues, and dried in vacuo. The product was formed quantitatively and in high purity as assessed by mass balance and NMR spectroscopy. Spectral data: $^1$H NMR (300 MHz, D$_2$O); δ 7.66–7.60 (m, 3H), 7.53–7.44 (m, 14H), 7.06 (d, J=8.0, 2H), 3.31–3.21 (m, 2H), 2.89 (t, J=6.9, 2H), 2.11 (s, 3H), 1.97–1.80 (m, 2H). $^{13}$C NMR (75.5 MHz, D$_2$O); δ 142.21, 139.75, 135.29, 135.25, 133.47, 133.34, 130.40, 130.23, 129.42, 125.44, 118.13, 116.98, 50.55, 50.33, 20.58, 20.04, 17.9.

Synthesis of Benzopinacolone (2,2,2-triphenylacetophenone)

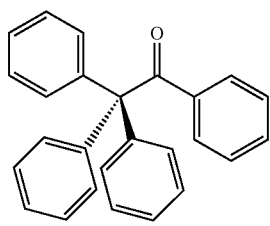

To a 5 mL reaction conical vial equipped with stir bar and reflux condenser was added 882 mg triphenyl(propyl-3-sulphonyl)phosphonium toluenesulfonate. Next added in one portion was 58.8 mg benzopinacole. The reaction was allowed to warm to 140° C. for a period of 2 hours. The resulting monophase was then allowed to cool to room temperature at which time the biphase was washed with EtOAc (3×2.0 mL) after addition of 1.0 mL water and 2.0 mL EtOAc. The combined organic phases were dried with anhydrous MgSO$_4$, filtered and concentrated in vacuo. The crude product (71.1 mg) revealed over a 99% conversion from benzopinacole to benzopinacolone via GC ((HP-1 methyl siloxane) 100° C. (2 min), 10° C./min, 275° C. (10 min)) 11.32 min (benzopinacole); 21.38 min (benzopinacolone). Purification by silica gel chromatography (EtOAc/Hex 1:8) afforded the desired material in 49.5 mg (88% isolated yield) as a white crystalline solid. Spectral data of this material matched that of commercially available material.

Syntheis of n-octyl Ether

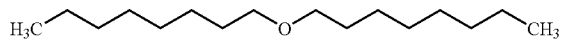

To a 5 mL reaction conical vial equipped with stir bar and reflux condenser was added 1.0 g (1.91 mmol) triphenyl (propyl-3-sulphonyl)phosphonium toluenesulfonate. Next added in one portion was 1.0 mL (6.35 mmol) 1-octanol. The reaction was allowed to warm to 175° C. over a period of 2 hours. The resulting monophase was then allowed to cool to room temperature at which time the biphase was washed with EtOAc (3×2.0 mL) after addition of 1.0 mL water and 2.0 mL EtOAc. The combined organic phases were dried with anhydrous MgSO$_4$, filtered and concentrated in vacuo. Purification by bulb-to-bulb distillation (bp 130° C./3 mm Hg (air bath temp)) afforded the desired material in 432 mg (56% isolated yield) as a clear and colorless oil.

The ratio of alcohol to IL effected the overall yield of octyl ether formation. From the combination of approximately 300 mg (0.57 mmol) triphenyl(propyl-3-sulphonyl) phosphonium toluenesulfonate and 0.45 mL 1-octanol, afforded was 55 mg (16% isolated yield), whereas from the combination of 771 mg (1.47 mmol) triphenyl(propyl-3-sulphonyl)phosphonium toluenesulfonate and 0.5 mL (3.18 mmol) 1-octanol, afforded was 96.8 mg (25% isolated yield). The products in each run were analyzed by GC ((HP-1 methyl siloxane) 100° C. (2 min), 10° C./min, 275° C. (10 min)) 4.83 min (1-octanol); 12.03 min (octyl ether) and confirmed by NMR. Spectral data of this material matched that of commercially available material.

Control Reaction using PTSA: From the combination of 1-octanol (0.5 mL, 3.17 mmol) and p-toluenesulfonic acid (280 mg, 1.47 mmol (using the monohydrate)) was obtained 187 mg n-octyl ether (49% isolated yield) based upon purification of the crude product by bulb-to-bulb distillation (bp 130° C./3 mm Hg (air bath temp)).

Control Reaction using NAFION 117: From the combination of 0.5 mL 1-octanol (3.17 mmol) and 0.314 g NAFION 117 (0.28 meq (0.89 meq/g)) in 3.0 mL toluene (1.1 M) as solvent was obtained 12.4 mg n-octyl ether (3% isolated yield) upon purification of the crude product (GC ratio of 90:10 (octanol:octyl ether)) by bulb-to-bulb distillation (bp 130° C./3 mm Hg (air bath temp)).

Synthesis of Pinacolone (3,3-dimethyl-2-butanone)

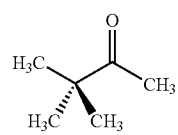

A 5 mL reaction conical vial was equipped with stir bar and Hinkman-Hinkle still head. Attached onto the still head was a reflux condenser with drying tube. To the reaction conical vial was added approximately 1.0 g triphenyl(propyl-3-sulphonyl)phosphonium toluenesulfonate. Next added in one portion to the reaction vial was 290 mg pinacol. The reaction was allowed to warm to a maximum temperature of 180° C. for a total period of 1 hour. The resulting monophase was then allowed to cool to room temperature at which time the distillate was transferred to another flask and analyzed by GC ((HP-1 methyl siloxane) 50° C. (2 min), 10° C./min, 275° C. (10 min)) 4.07 min (pinacolone); 6.17 min (pinacol) and NMR. Purification of the crude product via bulb-to-bulb distillation (bp 125° C./3 mm Hg (air bath temp)) afforded the desired material in 86 mg (35% isolated yield) as a clear and colorless oil. Spectral data of this material matched that of commercially available material.

Synthesis of 3-butyl-1-(butyl-4-sulfonyl)imidazolium trifluoromethanesulfonate

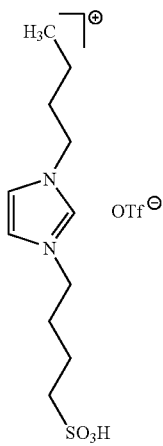

From the combination of 1-butylimidazole and 1,4-butane sultone was formed in excellent yield. After washing the salt with diethyl ether and toluene to remove any unreacted starting materials, the solid was dried in vacuo. Then, a stoichiometric amount of trifluoromethanesulfonic acid was added and the mixture stirred for two hours at 40° C. during which time the solid zwitterion dissolved/liquefied, resulted in the formation of 3-butyl-1-(butyl-4-sulfonyl)imidazolium trifluoromethanesulfonate. The IL phase was then washed repeatedly with toluene and ether to remove non-ionic residues, and dried in vacuo. The product was formed quantitatively and in high purity as assessed by mass balance and NMR spectroscopy. Spectral data: $^1$H NMR (300 MHz, D$_2$O); δ 8.68 (s, 1H), 7.40 (d, J=1.6, 1H), 7.39 (d, J=1.6, 1H), 4.13 (t, J=6.9, 2H), 4.08 (t, J=7.1, 2H), 2.82 (t, J=7.4, 2H), 1.91 (quint, J=8.0, 2H), 1.73 (q, J=7.7, 2H), 1.68–1.57 (m, 2H), 1.19 (dt, J=7.7, 7.7, 2H), 0.79 (t, J=7.4, 3H). $^{13}$C NMR (75.5 MHz, D$_2$O) δ 135.26, 122.64, 122.42, 119.80 (q, J$_{C-F}$=317.0, CF$_3$), 50.22, 49.49, 49.10, 31.31, 28.26, 21.11, 18.88, 12.75.

Synthesis of N-octyl hexanoate

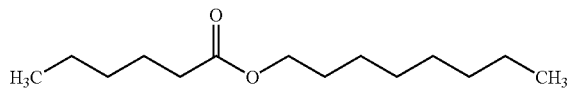

To a 5 mL reaction vial equipped with stir bar was added approximately 200 μL of 3-butyl-1-(butyl-4-sulfonyl)imidazolium trifluoromethanesulfonate (1.9 M). Added next via syringe was 1-octanol (60 μL, 0.38 mmol) followed by hexanoic acid (48 μL, 0.38 mmol). The resulting monophase was allowed to stir at room temperature for a period of 7 days at which time the oil was washed with toluene (5×2 mL). Shorter reaction times using higher reaction temperatures also afforded excellent conversion of acid to ester. Reaction of 1-octanol and acetic acid resulted in 89% conversion to n-octyl acetate at 40° C. for a period of 72 h whereas 83% conversion was observed at 40° C. for 48 h. The collected organic washes were concentrated in vacuo to afford 76 mg of n-octyl hexanoate. GC analysis of the crude product revealed only trace amounts of starting material in the organic washes. Purification of the crude colorless oil by bulb-to-bulb distillation afforded the desired compound in 72 mg (0.31 mmol, 82% yield) as a clear and colorless oil (bp 130° C./3 mm Hg (air bath temp)). $^1$H NMR (300 MHz, CDCl$_3$); δ 4.04, J=6.6, 2H), 2.27 (t, J=7.4, 2H), 1.63–1.58 (m, 4H), 1.30–1.25 (m, 14H), 0.87–0.80 (m, 6H). $^{13}$C NMR (75.5 MHz, CDCl$_3$); δ 174.10, 64.47, 34.42, 31.84, 31.39, 29.26, 28.72, 26.00, 24.78, 22.70, 22.38, 14.13, 13.96. IR (thin film) 2956, 2929, 2858, 1739, 1466, 1173 cm$^{-1}$. GC ((HP-1 methyl siloxane; f=1.0 mL/min) 100° C. (2 min), 10° C./min, 275° C. (10 min)) 11.05 min.

EXAMPLE 2

Reuse of a Brønsted Acid Ionic Liquid in the Formation of Ethyl Acetate

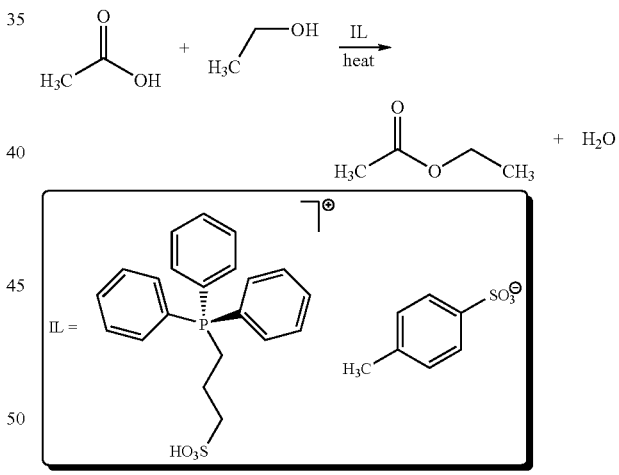

The reaction setup used to illustrate the reuse of the IL in synthetic transformations consisted of a 5 mL reaction conical vial equipped with a magnetic spin vane. Attached to the conical vial was a Hinkman-Hinkle still head which itself was equipped with a Claisen adapter and reflux condenser. Proper alignment of one of the two inlet ports of the Claisen adapter was essential for the addition of reagents via a syringe pump. The setup was equipped with a drying tube packed with CaCl$_2$ and heated externally via a sand bath.

Representative Procedure

To the 5 mL reaction conical vial charged with 2.1 g IL (4.0 mmol) was added via syringe acetic acid (1.0 mL, 17.5 mmol) and ethanol (1.0 mL, 17.5 mmol). The reaction mixture was allowed to warm to a maximum temperature of 175° C. (external temperature) over a period of 45 min. Although completion of reaction was observed prior to reaching the maximum temperature, reuse of the reaction setup/IL made it necessary to remove all volatile components via distillation prior to the next cycle. With each cycle, reaction completion was confirmed by GC analysis [GC ((HP-1 methyl siloxane; f=1.0 mL/min) 50° C. (2 min), 10° C./min, 275° C. (10 min)) 3.21 min (EtOH), 3.37 min (EtOAc), 3.42 min (AcOH)] and documented via the mass of distillate obtained. Each cycle afforded pure ethyl acetate without any appreciable amounts of starting material (<7% assuming loss of EtOH due to an EtOH/EtOAc azeotrope (31% by weight and bp of 78° C.)). Biphasic mixtures were separated and factored into product formation was maximum water content of 3.3%.

Control Reaction

A 5 mL reaction conical vial was charged with acetic acid (1.0 mL, 17.5 mmol) and ethanol (1.0 mL, 17.5 mmol). The reaction mixture was allowed to warm to a maximum temperature of 175° C. (external temperature) over a period of 45 min. Observed were no appreciable amounts of distillate even after continuous heating 30 min after the 45 min window. The distillate that was collected consisted of EtOH (97%) and EtOAc (7%). Remaining in the reaction conical vial was AcOH.

Regeneration and Subsequent Reuse of Ionic Liquid

The system after multiple cycles retained a significant amount of mass, primarily water, which correlated to a rise in mass percentage of over 151%. Based upon the mass balance of reaction cycles and product yields, the rise in mass consists of water and acetic acid. Removal of the VOCs using heat (<175° C.) at atmospheric pressure was unsuccessful. However, when the setup was evacuated (10 Torr) and warmed to 65° C. over a period of 5 hours, observed was the loss in volume contained in the reaction vial. The resulting ionic liquid still contained AcOH (42%) based upon $^1$H NMR analysis. Using the results from cycle 2, 0.441 mL of water was added prior to the addition of ethanol and acetic acid in an effort to mimic the water:IL ratio. This control experiment afforded 1.3 g ethyl acetate (87% isolated yield).

Tabulation of the Results from the Recycling the Brønsted Acidic Ionic Liquid

| cycle | ethyl acetate, %[a] |
|---|---|
| 1 | 82 |
| 2 | 91 |
| 3 | 96 |
| 4 | 81 |
| 5[b] | 87 |

[a]Isolated yield.
[b]Isolated yield using regenerated ionic liquid (addition of 0.441 mL water prior to run).

EXAMPLE 3

Synthesis and Characterization of Thioether IL 1 and Sulfoxide IL 1

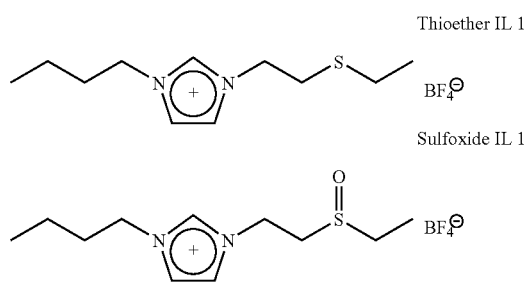

Part 1

A 250 mL round-bottomed flask was charged with a magnetic stirbar, 100 mL of toluene and 10.0 g (80.6 mmol) 1-butyl imidazole. To this solution was then added 10.4 g (80.6 mmol) of 2-(chloroethyl) ethyl sulfide. A condenser was fitted, and the solution heated to and maintained at reflux for 12 h. During this time, a dense yellow-brown liquid phase separated from the toluene. After cooling, the toluene layer was separated and discarded, and the lower, ionic liquid layer washed with 2×50 mL of diethyl ether. The viscous liquid was dried overnight in vacuo (15.2 g, 76%).

Part 2

The imidazolium chloride product from Part 1 (15.2 g, 61.1 mmol) was dissolved in 100 mL of acetonitrile and treated with 6.4 g (61.1 mmol of ammonium tetrafluoroborate, the suspension stirred overnight. The suspension was filtered and the solvent removed in vacuo to leave the tetrafluoroborate salt of the imidazolium cation (15.6 g, 85%).

Part 3

A 100 mL flask was charged with a stirbar and 1.52 g (5.3 mmol) of the tetrafluoroborate salt isolated in Part 2. This was then dissolved in 50 mL dichloromethane and the solution cooled to 0° C. To the cooled, stirred solution was added dropwise a solution of 1.38 g m-chloroperoxybenzoic acid (66.9% peroxide activity by assay, 3.9 mmol active peroxide) dissolved in 10 mL dichloromethane. The solution was allowed to warm to room temperature, during which time a white precipitate formed. The solvent was removed in vacuo, and the white solid residue extracted with 5×50 mL portions of ether. The by-product m-chlorobenzoic acid was completely extracted into the ether washings, leaving the pale-yellow liquid product.

Characterization Data for Sulfoxide IL 1

$^1$H NMR (300 MHz, CDCl$_3$, 25° C., TMS) δ 0.93 (t, 3H, CH$_3$), 1.31 (t, 3H, CH$_3$), 1.36 (m, 2H, CH$_2$), 1.84 (m, 2H, CH$_2$), 2.81 (complex m, 2H, CH$_2$), 3.17 (complex m, 1H, CH$_2$), 3.41 (complex m, 1H, CH2), 4.17 (t, 2H, CH$_2$), 4.73 (t, 2H, CH$_2$), 7.32 (m, 1H, ring CH), 7.60 (m, 1H, ring CH), 8.91 (s, 1H, ring CH). $^{13}$C NMR (75.56 MHz, CDCl$_3$, 25° C., $^1$H decoupled) δ 6.77, 13.42, 19.47, 31.84, 44.07, 46.05, 49.94, 50.10, 122.22, 123.42, 136.59.

Characterization Data for Thioether IL 1 (Product Produced in Part 2 Above)

$^1$H NMR (300 MHz, CDCl$_3$, 25° C., TMS) δ 0.88 (t, 3H, CH$_3$), 1.16 (t, 3H, CH$_3$), 1.30 (m, 2H, CH$_2$), 1.81 (m, 2H, CH$_2$), 2.50 (q, 2H, CH$_2$), 2.91 (t, 2H, CH$_2$), 4.15 (t, 2H, CH$_2$), 4.34 (t, 2H, CH$_2$), 7.36 (m, 1H, ring CH), 7.47 (m, 1H, ring CH), 8.77 (s, 1H, ring CH). $^{13}$C NMR (75.56 MHz, CDCl$_3$, 25° C., 1H decoupled) δ 13.37, 14.62, 19.35, 25.61, 31.57, 31.94, 49.05, 49.86, 122.38, 122.85, 136.00.

EXAMPLE 4

Synthesis and Characterization of Sulfone IL 1

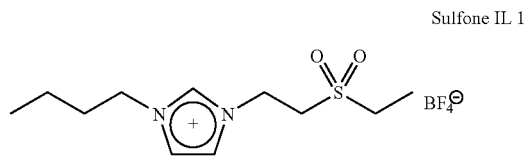

Sulfone IL 1

From Thioether IL 1. See Example 3.

A 100 mL flask was charged with a magnetic stirbar, 1.56 g (5.2 mmol) of the specified imidazolium tetrafluoroborate salt and 50 mL of dichloromethane. The solution was then cooled with an ice-water bath. To the cool, stirred solution was then added dropwise a solution of 2.82 g m-chloroperoxybenzoic acid (66.9% peroxide activity by assay, 5.2 mmol active peroxide) dissolved in 15 mL dichloromethane. The solution was allowed to warm to room temperature, during which time a white precipitate formed. The solvent was removed in vacuo, and the white solid residue extracted with 5×50 mL portions of ether. The by-product m-chlorobenzoic acid was completely extracted into the ether washings, leaving the pale-yellow liquid product that slowly crystallizes into a low-melting solid at room temperature. $^1$H NMR (300 MHz, DMSO-d$^6$, 25° C., TMS) δ 0.90 (t, 3H, CH$_3$), 1.23 (t, 3H, CH$_3$), 1.25 (m, 2H, CH$_2$), 1.75 (m, 2H, CH$_2$), 3.18 (q, 2H, CH$_2$), 3.78 (t, 2H, CH$_2$), 4.18 (t, 2H, CH$_2$), 4.64 (t, 2H, CH$_2$), 7.36 (m, 1H, ring CH), 7.47 (m, 1H, ring CH), 8.77 (s, 1H, ring CH). $^{13}$C NMR (75.56 MHz, DMSO-d$^6$, 25° C., 1H decoupled) δ 6.54, 13.78, 19.25, 31.82, 42.80, 47.51, 49.20, 50.25, 122.90, 123.22, 137.25.

EXAMPLE 5

Synthesis and Characterization of Thioether IL 2 and Sulfoxide IL 2

Part 1

A 100 mL round-bottomed flask was charged with a magnetic stirbar, 50 mL of toluene and 3.29 g (40 mmol) 1-methyl imidazole. To this solution was then added 5.0 g (40 mmol) of 2-(chloroethyl) ethyl sulfide. A condenser was fitted, and the solution heated to and maintained at reflux for 12 h. During this time, a dense yellow-brown liquid phase separated from the toluene. After cooling, the toluene layer was separated and discarded, and the lower, ionic liquid layer washed with 2×50 mL of diethyl ether. The viscous liquid was dried overnight in vacuo (7.41 g, 89%).

Part 2

The imidazolium chloride product from Part 1 (7.41 g, 35.8 mmol) was dissolved in 25 mL of acetonitrile and treated with 8.01 g (35.8 mmol of lithium bis(trifluoromethanesulfonylimide). The dissolution of the latter was quickly followed by the precipitation of LiCl. After stirring overnight, the suspension was filtered and the solvent removed in vacuo to leave the bis(triflyl)imide salt of the imidazolium cation (12.02 g, 86%).

Part 3

A 100 mL flask was charged with a stirbar and 1.51 g (3.9 mmol) of the product salt isolated in Part 2. This was then dissolved in 50 mL dichloromethane and the solution cooled to 0° C. To the cooled, stirred solution was added dropwise a solution of 1.00 g m-chloroperoxybenzoic acid (66.9% peroxide activity by assay, 3.9 mmol active peroxide) dissolved in 10 mL dichloromethane. The solution was allowed to warm to room temperature, during which time a white precipitate formed. After stirring for 12 h, the solvent was removed in vacuo, and the white solid residue extracted with 5×50 mL portions of ether. The by-product m-chlorobenzoic acid was completely extracted into the ether washings, leaving the pale-yellow liquid product.

Characterization Data for Sulfoxide IL 2

$^1$H NMR (300 MHz, CDCl$_3$, 25° C., TMS) δ 1.25 (t, 3H, CH$_3$), 2.79 (m, 2H, CH$_2$), 3.0–3.6 (complex m, 2H, CH$_2$), 3.86 (s, 3H, CH$_3$), 4.63 (m, 2H, CH$_2$), 7.35 (m, 1H, ring CH), 7.52 (m, 1H, ring CH), 8.76 (s, 1H, ring CH).

Characterization Data for Thioether IL 2 (Product of Part 2 Above)

$^1$H NMR (300 MHz, CDCl$_3$, 25° C., TMS) δ 1.21 (t, 3H, CH$_3$), 2.51 (m, 2H, CH$_2$), 2.91 (m, 2H, CH$_2$), 3.90 (s, 3H, CH$_3$), 4.34 (m, 2H, CH$_2$), 7.32 (m, 1H, ring CH), 7.41 (m, 1H, ring CH), 8.65 (s, 1H, ring CH). $^{13}$C NMR (75.56 MHz, CDCl$_3$, 25° C., $^1$H decoupled) δ 14.49, 25.80, 31.55, 36.43, 49.21, 120.00 (q, CF$_3$), 122.81, 123.72, 136.23.

EXAMPLE 6

Synthesis and Characterization of Sulfone IL 2

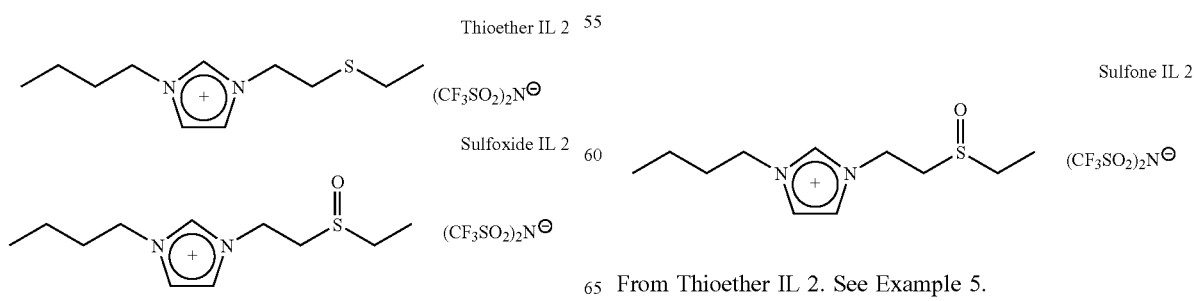

From Thioether IL 2. See Example 5.

In a 100 mL flask charged with a magnetic stirbar, 1.50 g (3.9 mmol) 1-methyl-3-(2-ethylsufido)ethyl imidazolium bif (triflyl)imide [product of Part 2 above] was dissolved in 50 mL dichloromethane and the solution cooled in an ice bath. To the cooled, stirred solution was added dropwise a solution of 1.99 g m-chloroperoxybenzoic acid (66.9% peroxide activity by assay, 7.8 mmol active peroxide) dissolved in 20 mL dichloromethane. The solution was allowed to warm to room temperature, during which time a white precipitate formed. After stirring for 14 h, the solvent was removed in vacuo, and the white solid residue extracted with 5×50 mL portions of ether. The by-product m-chlorobenzoic acid was completely extracted into the ether washings, leaving the pale-yellow liquid product. $^1$H NMR (300 MHz, CDCl$_3$, 25° C., TMS) δ 1.26 (t, 3H, CH$_3$), 3.06 (q, 2H, CH$_2$), 3.58 (m, 2H, CH$_2$), 3.82 (s, 3H, CH$_3$), 4.61 (m, 2H, CH$_2$), 8.58 (br s, 2H, ring CH), 8.98 (s, 1H, ring CH). $^{13}$C NMR (75.56 MHz, DMSO-d$^6$, 25° C. $^1$H decoupled) δ 6.54, 36.11, 42.80, 47.00, 49.20, 50.05, 120.00 (q, CF$_3$), 123.18, 124.15, 137.82.

EXAMPLE 7

Synthesis and Characterization of Thioether IL 3 and Sulfoxide IL 3

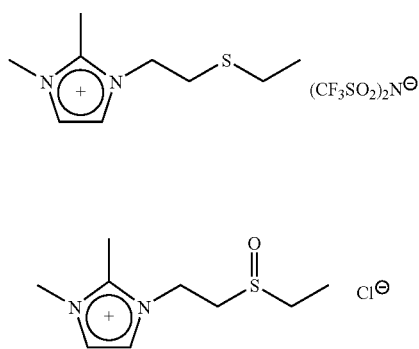

Thioether IL 2

Sulfoxide IL 2

Part 1

A 250 mL round-bottomed flask was charged with a magnetic stirbar, 75 mL of toluene and 11.55 g (120 mmol) 1,2-dimethyl imidazole. To this solution was then added 14.97 g (120 mmol) of 2-(chloroethyl) ethyl sulfide. A condenser was fitted, and the solution heated to and maintained at reflux for 12 h. During this time, a dense yellow-brown liquid phase separated from the toluene. After cooling, the toluene layer was separated and discarded, and the lower, ionic liquid layer washed with 2×50 mL of diethyl ether. The viscous liquid was dried overnight in vacuo, solidifying during that time into a low-melting, tan crystalline solid. (18.06 g, 68%).

Part 2

The imidazolium chloride product from Part 1 (7.70 g, 35.0 mmol) was dissolved in 25 mL of acetonitrile and treated with 10.04 g (35.0 mmol of lithium bis(trifluoromethanesulfonylimide). The dissolution of the latter was quickly followed by the precipitation of LiCl. After stirring overnight, the suspension was filtered and the solvent removed in vacuo to leave the bis(triflyl)imide salt of the imidazolium cation (12.20 g, 75%).

Part 3

A 100 mL flask was charged with a stirbar and 4.35 g (19.8 mmol) of the chloride salt isolated in Part 1. This was then dissolved in 50 mL dichloromethane and the solution cooled to 0° C. To the cooled, stirred solution was added dropwise a solution of 5.10 g m-chloroperoxybenzoic acid (66.9% peroxide activity by assay, 19.8 mmol active peroxide) dissolved in 10 mL dichloromethane. The solution was allowed to warm to room temperature and stir for 12 h, after which time the solvent was removed in vacuo, and the white solid residue extracted with 5×50 mL portions of ether. The by-product m-chlorobenzoic acid was completely extracted into the ether washings, leaving the pale-yellow glass that was shown by NMR to still contain m-chlorobenzoic acid. The glass was then dissolved in 50/50 (v/v) acetonitrile/methanol and chromatographed on silica gel. Elution of a pale yellow band gave the product IL sulfoxide chloride salt as a yellow glass that liquefies upon modest heating (2.4 g, 50%).

Characterization Data for Sulfoxide IL 3

$^1$H NMR (300 MHz, CDCl$_3$, 25° C., TMS) δ 1.32 (t, 3H, CH$_3$), 2.72–3.06 (complex m, 2H, CH$_2$), 2.86 (s, 3H, CH$_3$), 3.20 (m, 1H, CH), 3.86 (m, 1H, CH); 3.93 (s, 3H, CH$_3$), 4.68–4.92 (complex m, 2H, CH$_2$), 7.62 (d, 1H, CH), 8.60 (d, 1H, CH).

Characterization Data for Thioether IL 3 (Product of Part 2 Above)

$^1$H NMR (300 MHz, CDCl$_3$, 25° C., TMS) δ 1.28 (t, 3H, CH$_3$), 2.54 (m, 2H, CH$_2$), 2.26 (s, 3H, CH3), 2.90 (m, 2H, CH$_2$), 3.81 (s, 3H, CH$_3$), 4.50 (m, 2H, CH$_2$), 7.22 (d, 1H, ring CH), 7.27 (d, 1H, ring CH).

EXAMPLE 8

Preparation and Characterization of Sulfoxide IL 4

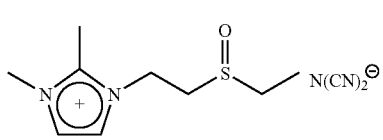

Sulfoxide IL 4

A 50 mL flask was charged with a magnetic stirbar, 1.0 g (4.2 mmol) of Sulfoxide IL 3 (Example 8) and 10 mL of deionized water. In a separate flask sheilded from light, 0.40 g (4.5 mmol) sodium dicyanamide was dissolved in 10 mL of deionized water. To this solution was added 0.77 g (4.5 mmol) silver nitrate, and the solution stirred for four hours. At the end of this period, the suspended solid (AgC$_2$N$_3$) was quickly recovered by filtration, washed with a small portion of water, and added into the flask containing Sulfoxide IL 3. This flask was stirred in the dark for two hours, after which time the precipitated silver chloride was removed by filtration. Removal in vacuo of the water from the yellow-orange solution gave the viscous yellow-brown liquid product (0.95 g, 3.6 mmol, 85%). $^1$H NMR (300 MHz, CDCl$_3$, 25° C., TMS) δ 1.30 (t, 3H, CH$_3$), 2.68–3.01 (complex m, 2H, CH$_2$), 2.86 (s, 3H, CH$_3$), 3.22 (m, 1H, CH), 3.90 (m, 1H, CH); 3.91 (s, 3H, CH$_3$), 4.61–4.90 (complex m, 2H, CH$_2$), 7.58 (d, 1H, CH), 8.47 (d, 1H, CH).

EXAMPLE 9

Preparation and Characterization of Sulfoxide IL 5

Sulfoxide IL 5

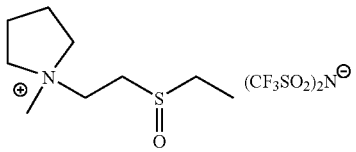

Part 1

A 100 mL flask was charged with a magnetic stirbar and 8.0 g (94 mmol) N-methyl pyrrolidine. To the amine was added 40 mL of acetonitrile and 14.0 g (96 mmol) 2-chloroethyl ethyl sulfide. The solution was then heated at reflux for 24 h, after which time the volatiles were removed in vacuo. The sticky tan-brown residue was repeatedly washed with small portions of toluene and then ether. The impure product was taken up into 50/50 v/v acetonitrile/methanol and filtered through a short silica column. The solvent was removed in vacuo leaving a tan solid (5.9 g, 27%, unoptimized).

Part 2

A 100 mL flask was charged with a stirbar and 2.0 g (8.6 mmol) of the pyrrolidinium chloride salt isolated from Part 1. To this solid was added 25 mL of acetonitrile and 2.5 g (8.6 mmol) lithium bis(trifluoromethylsulfonyl)imide. The dissolution of the latter was followed by precipitation of lithium chloride, which was removed by filtration. Evaporation of the acetonitrile gave a viscous, pale yellow liquid (3.3 g, 80%).

Part 3

The product isolated from Part 2 (6.9 mmol) was dissolved in 50 mL dichloromethane in a 100 mL flask that had also been charged with a magnetic stirbar. To this stirred solution was added 1.78 g of m-chloroperoxybenzoic acid (66.9% peroxide activity by assay, 6.9 mmol active peroxide) dissolved in 10 mL dichloromethane. The solution was stirred overnight, during which time a white solid formed. The solvent was removed in vacuo and the white solid residue extracted with 4×50 mL portions of ether. The by-product m-chlorobenzoic acid was extracted into the ether washings, leaving a viscous, colorless liquid product.

EXAMPLE 10

Synthesis and Characterization of THF-Appended Ionic Liquid 1

THF-IL 1

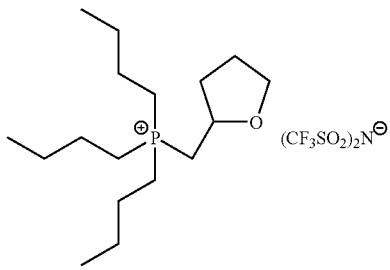

Part 1

Under an atmosphere of argon, a 100 mL flask equipped with a stirbar and fitted with a reflux condenser was charged with 10.0 g of a 50 wt. % solution of tributylphosphine (24.6 mmol phosphine) in toluene. While maintaining the inert atmosphere, 3.0 g (25.0 mmol) tetrahydrofurfuryl chloride was added and the solution brought to reflux. After 12 h, a white solid had precipitated which was isolated by filtration (7.49 g, 94%).

Part 2

The solid chloride salt isolated in Part 1 was dissolved in 75 mL of acetonitrile, giving a colorless solution. To this stirred solution was added 6.64 g (23 mmol) of lithium bis(trifluoromethylsulfonyl)imide. Dissolution of the former in the acetonitrile was followed in a short period of time by the precipitation of lithium chloride. After stirring for two hours, the solid was removed by filtration and the solvent stripped in vacuo. The residual colorless oil was washed with 3×20 mL of ether and dried in vacuo, leaving a colorless oil (10.8 g, 82%).

Characterization Data for THF-IL 1

$^1$H NMR (300 MHz, CDCl$_3$, 25° C., TMS) δ 0.95 (t, 9H, CH$_3$), 1.51 (br, unresolved m, 12H, CH$_2$), 1.62–2.62 (br, complex overlapping m, 12H, CH$_2$), 3.4–3.9 (overlapping m, 2H, CH$_2$), 4.18 (br, 1H).

EXAMPLE 11

Synthesis and Characterization of THF-Appended IL 2

THF-IL 2

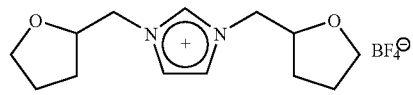

In a 250 mL flask equipped with a magnetic stirbar, 10.0 g (99 mmol) of furfuryl amine was dissolved in 100 mL of deionized water. To the stirred solution was added 18.1 g of a 48 wt. % solution of tetrafluoroboric acid in water (99 mmol acid). After stirring for two days, 1.49 g (49.5 mmol) of powdered formaldehyde was added to the yellow solution, which was then heated to 70° C., at which point the mixture became homogeneous. The solution was then cooled to room temperature, at which point 7.2 g of 40% aqueous glyoxal (49.5 mmol glyoxal) was added and stirring continued for 3 h during which time the solution became orange-brown in color. The aqueous solution was then extracted with three 100 mL portions of dichloromethane, which were then combined and dried over magnesium sulfate. The solid was then removed by filtration and the solvent removed in vacuo, leaving a relatively mobile redbrown liquid 11.6 g (38 mmol, 76%).

Characterization Data $^1$H NMR (300 MHz, CDCl$_3$, 25° C., TMS; mixture of all diastereoisomers; relative integrations) δ 1.56 (m, 2H, CH$_2$), 1.90 (m, 4H, CH$_2$), 2.13 (m, 2H, CH$_2$), 3.79 (m, 2H, CH$_2$), 3.86 (m, 2H, CH$_2$), 4.06 (m, 2H, CH$_2$), 4.17 (m, 2H, CH2), 4.37 (m, 2H, CH), 7.44 (m, 2H, ring CH), 8.77 and 8.79 (singlets, 1H, ring CH).

EXAMPLE 12

Synthesis and Characterization of Cyclic Amide Appended IL 1

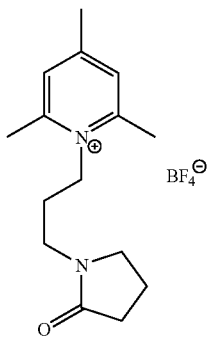

Cyclic amide IL 1

In a 100 mL flask charged with a stirbar and flushed with argon, 5.0 g (23.8 mmol) of 2,4,6-trimethylpyrylium tetrafluoroborate was suspended in 40 mL of dichloromethane. To the stirred suspension was added 3.4 g (24 mmol) N-(3-aminopropyl) pyrrolidinone. The suspension was stirred overnight at 40° C., during which time the starting tetrafluoroborate salt dissolved and a red-orange solution was obtained. The solvent was removed in vacuo, producing a sticky brown solid. The solid was dissolved in 30 mL of acetonitrile and flash filtered through a short plug of silica gel, the silica retaining some degree of color. The collected eluant was evaporated, leaving a red-brown oil. $^1$H NMR (300 MHz, CDCl$_3$, 25° C., TMS) δ 2.04 (m, 4H, CH$_2$), 2.33 (m, 2H, CH$_2$), 2.49 (s, 3H, CH$_2$), 2.79 (s 6H, CH$_3$), 3.47 (overlapping m, 6H, CH$_2$), 7.46 (s, 2H, CH).

EXAMPLE 13

Synthesis and Characterization of Cyclic Amide Appended IL 2

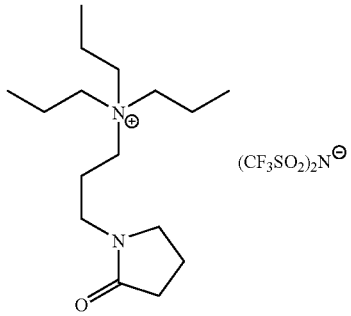

Cyclic amide IL 2

Part 1

A 250 mL flask fitted with a reflux condenser is charged with a stirbar, 100 mL of acetonitrile, and 5 g (35 mmol) N-(3-aminopropyl) pyrrolidinone. To the stirred solution is added 17 g of sodium bicarbonate (excess) and 26.6 g (158 mmol) propyl iodide. The solution/suspension was heated to reflux for 12 h. After cooling, the solids were removed by filtration and the solvent removed in vacuo, leaving a tan solid. The solid was spectroscopically determined to be impure. It was then dissolved in 10 mL of acetonitrile, and loaded onto a silica column (2 cm×16 cm). The column was eluted with a solvent gradient that changed from pure acetonitrile to pure methanol. The product eluted with the methanol rich fraction. The solvent was removed in vacuo, leaving a white solid (6.8 g, 20 mmol, 57%).

Part 2

The product from Part 1 was dissolved in 50 mL of acetonitrile and treated with 5.7 g (20 mmol) lithium bis(trifluoromethylsulfonyl)imide. Within a short time, the latter had dissolved and this was then followed by the precipitation of lithium chloride. After stirring overnight, the solid was removed by filtration and the solvent removed in vacuo, leaving a colorless viscous liquid.

Characterization Data $^{13}$C NMR (75.56 MHz, CDCl$_3$, 25° C., $^1$H decoupled) δ 10.96, 15.99, 18.16, 21.36, 31.07, 40.07, 48.30, 57.58, 60.92, 121.02 (q, CF$_3$), 176.19.

EXAMPLE 14

Synthesis and Characterization of Acyclic Amide IL 1

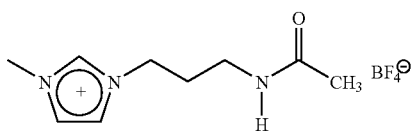

Acyclic amide IL 1

Part 1

In a 250 mL flask charged with a stirbar and flushed with argon, 10.0 g (80 mmol) N-(3-aminopropyl) imidazole was dissolved in 100 mL of diethyl ether. To the stirred solution was added dropwise 6.3 g (80 mmol) acetyl chloride. Within seconds the solution became cloudy as the hydrochloride salt of the acetylamino propyl imidazole salt precipitated. After stirring for 1 h, the product was isolated by filtration, washed with 2×10 mL of ether and dried in vacuo (16.2 g, 80 mmol, 100%).

Part 2

The hydrochloride salt isolated in Part 1 was dissolved in 25 mL of water, and a stoichiometric quantity of solid sodium hydroxide pellets added in small portions, taking care that the solution temperature did not exceed 50° C. Some granular crystalline solid formed as the reaction proceeded. After 3 h, the solution was extracted with 3×100 mL of dichloromethane. The extracts were combined, dried over anhydrous magnesium sulfate and the solvent removed in vacuo. The isolated product was a colorless liquid (11.7 g, 88%).

Part 3

The acetylated imidazole product isolated in Part 2 (70 mmol) was dissolved in 50 mL of dichloromethane in a flask fitted with a magnetic stirbar and reflux condenser. To the stirred solution was added 10.0 g (70.4 mmol) methyl iodide. The solution was heated to 40° C. for 12 h, after which time the solvent and excess methyl iodide were removed in vacuo. The residue was washed with 2×25 mL of ether and dried in vacuo, leaving a colorless semi-solid (21 g, 68 mmol).

Part 4

The product of Part 3 (21 g) was dissolved in 100 mL of acetonitrile and 7.5 g (72 mmol) ammonium tetrafluoroborate added as a solid. The resulting suspension was stirred overnight, after which time the solvent was removed in vacuo. The sticky residue was extracted with 4×100 mL of dichloromethane, and the solids removed by filtration. Removal of the solvent in vacuo yielded the desired product as a viscous liquid (21.1 g, 78%).

Characterization Data $^1$H NMR (300 MHz, CDCl$_3$, 25° C., TMS; some peaks are doubled due to the observation of both amide rotamers) δ 2.07 and 2.08 (s, 3H, CH$_3$), 2.19–2.29 (overlapping m, 2H, CH$_2$), 3.28 (overlapping q, 2H, CH$_2$), 4.05 (s, 3H, CH$_3$), 4.45 (t, 2H, CH$_2$), 7.25 (m, 1H, ring CH), 7.58 (m, 1H, ring CH), 7.65 (br s, 1H, N—H), 9.79 (s, 1H, ring CH).

EXAMPLE 15

Synthesis and Characterization of Acyclic Amide IL 2

Acyclic amide IL 2

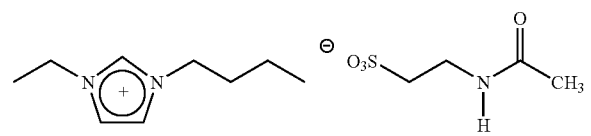

In a 250 mL flask charged with a magnetic stirbar, 10.0 g (36 mmol) of 1-butyl-3-ethyl imidazolium iodide was dissolved in 50 mL of deionized water. To the stirred solution was added 7.0 g (36 mmol) of sodium N-acetyl taurine. The solution was stirred overnight, and the water removed in vacuo. The gummy residue was extracted with 2×100 mL acetonitrile, the solids removed by filtration, and the acetonitrile removed in vacuo, leaving the product as a stiff glass (9.6 g, 84%).

Characterization Data $^1$H NMR (300 MHz, D$_2$O, 25° C.) δ 0.88 (t, 3H, CH$_3$), 1.26 (m, 2H, CH$_2$), 1.45 (t, 3H, CH$_3$), 1.80 (m, 2H, CH$_2$), 1.95 (s, 3H, CH$_3$), 3.04 (m, 2H, CH$_2$), 3.53 (m, 2H, CH$_2$), 4.15 (complex, overlapping m, 4H, CH$_2$), 7.44 (m, 2H, CH), 8.72 (s, 1H, CH); amide N—H not obsvd (D$_2$O solvent).

EXAMPLE 16

Synthesis and Characterization of Acyclic Amide IL 3, Comprising a Urea Functional Group Acyclic amide IL 3

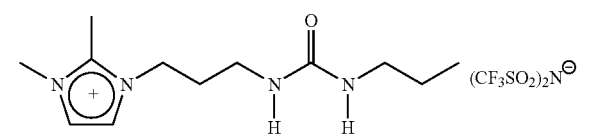

In a 100 mL flask charged with a magnetic stirbar and maintained under an argon atmosphere, 3.0 g (21 mmol) of 1-(3-aminopropyl)-2-methyl imidazole was dissolved in 25 mL of dichloromethane. To the stirred solution was added 1.8 g (22 mmol) n-propylisocyanate. After stirring for 3 h, the dichloromethane was removed in vacuo, leaving a thick oil (4.7 g, 99%). The oil was subsequently redissolved in 50 mL of acetonitrile and 3.0 g (22 mmol) methyl iodide added. The solution was warmed to 40° C. and stirred at that temperature overnight [caution—overheating can result in the formation of undesired by-products from O-alkylation]. After cooling, 6.02 g of lithium bis(trifluoromethylsulfonylimide) was added. Stirring was continued for an additional four hours, and the solvent then removed in vacuo. The brown residue was extracted with 4×100 mL of dichloromethane, filtered and the solvent again removed in vacuo, leaving a yellow oil (7.6 g, 66%).

Characterization Data $^1$H NMR (300 MHz, CD$_3$CN 25° C., TMS) δ 0.89 (t, 3H, CH$_3$), 1.24–1.44 (complex m, 2H, CH$_2$), 1.81–1.95 (complex m, 2H, CH2), 2.26 (s, 3H, CH3), 3.05 (m, 4H, CH2), 4.10 (m, 2H, CH2), 3.81 (s, 3H, CH$_3$), 5.15 (br s, 1H, NH), 5.25 (br s, 1H, CH), 7.36 (d, 1H, ring CH), 7.46 (d, 1H, ring CH).

EXAMPLE 17

Synthesis and Characterization of Amine Appended IL 1

Amine IL 1

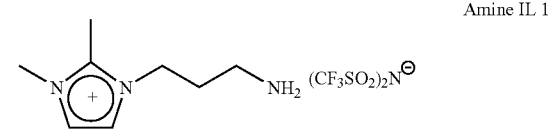

In a 500 mL flask charged with a magnetic stirbar and fitted with a reflux condenser, 26.0 g (270 mmol) 1,2-dimethyl imidazole was dissolved in 200 mL of absolute ethanol. To the stirred solution was added 58.6 g (270 mmol) 3-bromopropyl amine hydrobromide. The solution was stirred under reflux for 12 h, during which time a copious amount of solid precipitated. The solvent was then removed in vacuo, leaving a sticky white mass. This resudue was dissolved in 150 mL distilled water, and then 10.8 g of solid sodium hydroxide added in small portions with stirring. The solution became warm, and slowly precipitated a colorless granular solid. After one hour, the water was removed in vacuo, and the residue extracted into methanol, filtered, and the solvent again removed in vacuo, leaving a stiff yellow glass (59.9 g, 95%). The glass from the previous step was redissolved in 200 mL of methanol, and 73.5 g (255 mmol) lithium bis(trifluoromethylsulfonyl)imide added as a solid. After stirring overnight, the solvent was removed in vacuo and the residue extracted with 3×100 mL of 50/50 dichloromethane/ethanol. The solids were removed by filtration, and the solvent removed in vacuo, leaving a yellow liquid (82.3 g, 190 mmol, 75%).

Characterization Data for Amine IL 1

$^1$H NMR (300 MHz, CD$_3$OD, 25° C., TMS) δ 2.01 (m, 2H, CH$_2$), 2.56 (s, 3H, CH$_3$), 2.80 (m, 2H, CH$_2$), 3.72 (s, 2H, CH$_2$), 4.15 (m, 2H, CH$_2$), 7.29 (d, 1H, CH), 7.30 (d, 1H, CH); NH obsvd as a broad lump in the baseline around 4 ppm.

EXAMPLE 18

Synthesis and Characterization of Amine Appended IL 2

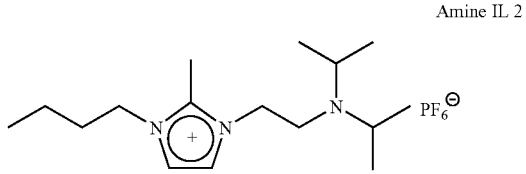

Amine IL 2

In a 100 mL flask fitted with a stirbar and reflux condenser, 5.0 g (36 mmol) of 1-butyl-2-methyl imidazole was dissolved in 40 mL of absolute ethanol. To the stirred solution was added in one portion 10.3 g (36 mmol) of N-(2-bromoethyl) diisopropyl amine hydrobromide. The resulting solution was heated under reflux for twelve hours, after which time 1.5 g (36 mmol) of sodium hydroxide was added and stirring continued for an additional four hours. The solution was filtered and the solvent removed in vacuo, leaving a pale yellow mass. The residue was subsequently dissolved in 100 mL of methanol, and then 2 mL of water and 8.0 g (excess) potassium hexafluorophosphate was added. After stirring overnight, the suspended solids were removed by filtration and the solvent removed in vacuo. The residue was re-extracted into dichloromethane, the suspended solids removed by filtration and the solvent removed in vacuo, leaving the product as a yellow oil (9.5 g, 64%).

Characterization Data $^1$H NMR (300 MHz, CDCl$_3$, 25° C., TMS) δ 0.82 (overlapping m, 15H, CH$_3$), 1.37 (m, 2H, CH), 1.79 (m, 2H, CH$_2$), 2.54 (s, 3H, CH$_3$), 2.78 (m, 2H, CH$_2$), 2.94 (m, 2H, CH$_2$), 4.11 (m, 4H, CH$_2$), 7.27 (d, 1H, CH), 7.33 (d, 1H, CH).

EXAMPLE 19

Synthesis and Characterization of Amine Appended IL 3

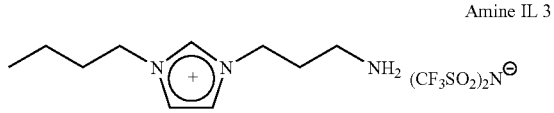

Amine IL 3

In a 250 mL flask charged with a magnetic stirbar and fitted with a reflux condenser, 10.0 g (81 mmol) 1-butyl imidazole was dissolved in 100 mL of absolute ethanol. To the stirred solution was added 17.5 g (81 mmol) 3-bromopropyl amine hydrobromide. The solution was stirred under reflux for 12 h, during which time a copious amount of solid precipitated. The solvent was then removed in vacuo, leaving a sticky white mass. This resudue was dissolved/suspended in 100 mL of methanol, and then 3.2 g of solid sodium hydroxide added in small portions with stirring. After four hours, the suspension was filtered and the solvent was removed in vacuo. The residue was extracted into acetonitrile (100 mL) and 23.1 g lithium bis(trifluoromethylsulfonyl)imide added as a solid. After stirring overnight, the solvent was removed in vacuo and the residue extracted with 3×50 mL of 75/25 (v/v) dichloromethane/ethanol. The solids were removed by filtration, and the solvent removed in vacuo, leaving a yellow liquid (17.3 g, 42%).

Characterization Data $^1$H NMR (300 MHz, CDCl$_3$, 25° C., TMS) δ 0.88 (t, 3H, CH$_3$), 1.29 (m, 4H, CH$_2$), 2.07 (m, 2H, CH$_2$), 2.70 (m, 2H, CH$_2$), 4.01 (br s, 2H, NH$_2$), 4.20 (m, 2H, CH$_2$), 4.43 (m, 2H, CH2), 7.49 (d, 1H, CH), 7.58 (d, 1H, CH), 8.98 (s, 1H, CH).

EXAMPLE 20

Synthesis and Characterization of Amine Appended IL 4

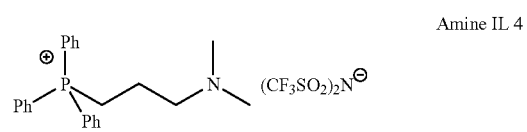

Amine IL 4

Under an argon atmosphere in a 100 mL flask equipped with a magnetic stirbar and reflux condenser, 5.0 g (19 mmol) triphenylphosphine was dissolved/suspended in 50 mL of absolute ethanol. To the stirred solution was added 4.7 g (19 mmol) N-(3-bromopropyl) dimethyl amine hydrobromide. The mixture was stirred under reflux for twenty four hours, after which time the solvent was removed in vacuo. The solid was dissolved in 50 mL of water, and 1 M aqueous sodium hydroxide added until the solution pH reached 8.5. The aqueous solution was then extracted with 3×100 mL of dichloromethane. The organic extracts were combined, dried over anhydrous magnesium sulfate and filtered. Removal of the solvent in vacuo gave a colorless glass (3.3 g). The glass was dissolved in 60 mL of acetonitrile, and 2.4 g (7.8 mmol) lithium bis(trifluoromethylsulfonyl)amide added as a solid. The solution was stirred overnight, after which time the solution was filtered and the solvent was removed in vacuo, leaving the product as a viscous liquid (4.7 g, 42% overall).

Characterization Data $^1$H NMR (300 MHz, CDCl$_3$, 25° C., TMS) δ 1.85 (m, 2H, CH$_2$), 2.23 (s, 6H, CH$_3$), 2.60 (m, 2H, CH$_2$), 3.36 (m, 2H, CH$_2$), 7.64–7.74 (m, 12H, CH), 7.77–7.87 (m, 3H, CH).

EXAMPLE 21

Synthesis and Characterization of Amine Appended IL 5

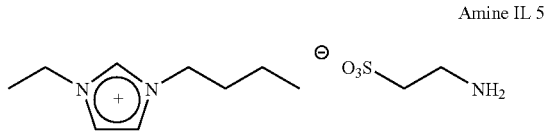

Amine IL 5

In a 100 mL flask equipped with a magnetic stirbar, 4.0 g (14 mmol) 1-butyl-3-ethyl imidazolium iodide was dissolved in 50 mL of absolute ethanol. To the stirred solution was added 2.10 g (slight excess) of solid sodium tauride. The solution/suspension was stirred overnight, after which time the suspended solids were filtered and the solvent removed from the filtrate under vacuum (1.5 g, 38%).

Characterization Data $^1$H NMR (300 MHz, CDCl$_3$, 25° C., TMS) δ 0.97 (overlapping t, 6H, CH$_3$), 1.40 (m, 2H, CH$_2$), 1.62 (overlapping m, 6H), 1.91 (m, 2H, CH2), 4.35 (m, 2H, CH$_2$), 4.45 (m, 2H, CH$_2$), 7.34 (m, 1H, ring CH), 7.40 (m, 1H, ring CH), 10.26 (s, 1H, ring CH). $^{13}$C NMR (75.56 MHz, D$_2$O, 25° C., $^1$H decoupled) δ 13.01, 14.83, 19.07, 31.51, 36.74, 45.08, 49.57, 53.37, 122.18, 122.52, 136.23.

EXAMPLE 22

Synthesis and Characterization of Amine Appended IL 6

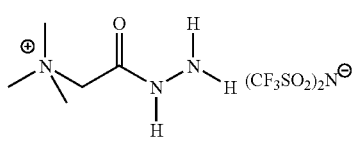

Amine IL 6

In a 100 mL flask equipped with a magnetic stirbar, 10.0 g (60 mmol) of Girard's Reagent T [(carboxymethyl)trimethyl ammonium chloride hydrazide] was dissolved/suspended in 50 mL of 1:1 (v/v) acetonitrile/methanol. To the stirred solution was added 17.1 g (60 mmol) lithium bis(trifluoromethylsulfonyl)imide. After stirring overnight, the solvent was removed in vacuo. The residue was extracted with 2×50 mL of acetonitrile, filtered and evaporated to leave a colorglass that solidifies on standing into a low-melting solid (22.3 g, 90%).

Characterization Data $^1$H NMR (all peaks, combined rotomers (300 MHz, D$_2$O, 25° C.) δ 1.97 (s), 2.02 (s), 2.04 (s), 2.18 (s), 3.26 (s), 3.30(s), 4.05 (s), 4.21 (s).

EXAMPLE 23

Synthesis and Characterization of Amine Appended IL 7

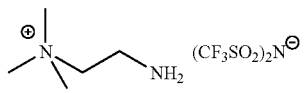

Amine IL 7

In a 100 mL flask equipped with a magnetic stirbar, 5.0 g (29 mmol) of (2-aminoethyl)-trimethylammonium chloride hydrochloride was dissolved/suspended in 50 mL of deionized water. The pH of the aqueous phase was adjusted to pH 8.5 by the addition of 1 M sodium hydroxide. To the stirred solution was added 8.6 g (30 mmol) lithium bis(trifluoromethylsulfonyl)imide, and the solution stirred overnight. The water was removed in vacuo, and the residue extracted with 3×100 mL of 1:1 (v/v) absolute ethanol/acetonitrile. The combined extracts were filtered through paper, then flash filtered through a short plug of silica gel. Evaporation of the eluate gave the product as a glass (7.97 g, 66%).

EXAMPLE 24

Synthesis and Characterization of Fluoro Alcohol IL 1

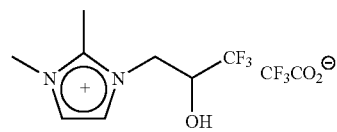

Fluoro alcohol IL 1

In a 50 mL flask equipped with magnetic stirbar and a reflux condenser, 1.0 g (5.2 mmol) of 3-bromo-1,1,1-trifluoro-2-propanol was dissolved in 15 mL of acetonitrile. To this solution was added 1.5 g (slight excess) of 1,2-dimethyl imidazole. The mixture was stirred under reflux overnight, after which time the volatiles were removed in vacuo. The residues were chromatographed on silica gel, beginning with acetonitrile and eluting in a gradient fashion with increasing proportions of methanol. The desired bromide salt eluted with the methanol rich fractions. Removal of the solvent in vacuo left a yellow glass (0.43 g, 17%). The glass was subsequently dissolved in 25 mL of acetone, and 0.20 g (0.88 mmol) silver trifluoroacetate added as a solid. The solution was stirred in the dark for one hour, after which time it was filtered and the solvent removed in vacuo, leaving the product as a yellow oil (0.51 g, 98%).

Characterization Data $^1$H NMR (300 MHz, CDCl$_3$, 25° C., TMS) δ 2.70 (s, 3H, CH$_3$), 3.80 (s, 3H, CH$_3$), 4.18 (m, 1H, CH or CH$_2$), 4.37 (m, 1H, CH or CH$_2$), 4.63 (m, 1H, CH or CH$_2$), 7.19 (d, 1H, CH), 7.40 (m, 1H, CH), 7.74 (br, 1H, OH).

EXAMPLE 25

Synthesis and Characterization of Fluoroketone IL 1

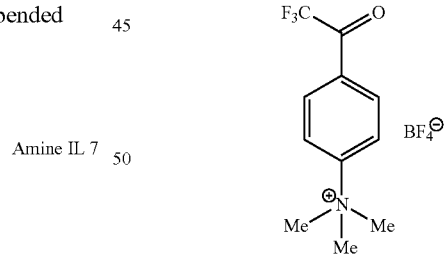

Fluoro ketone IL 1

Under a nitrogen atmosphere in a 100 mL flask equipped with a magnetic stirbar, 5.0 g (22.8 mmol) was suspended in 50 mL of dichloromethane. To the stirred solution was added 3.4 g (22.8 mmol) trimethyl oxonium tetrafluoroborate, and the solution/suspension stirred overnight. Removal of the volatiles in vacuo left a low-melting solid (5.15 g, 96%).

Characterization Data $^1$H NMR (300 MHz, DMSO-d$^6$, 25° C., TMS) δ 3.67 (s, 9H, CH$_3$), 7.83 (d, 2H, CH), 8.00 (d, 2H, CH). $^{13}$C NMR (75.56 MHz, DMSO-d$^6$, 25° C., $^1$H decoupled) δ 56.93, 92.66 (q, CF coupled), 120.62, 124.20 (q, CF coupled), 129.59, 140.99, 148.22.

EXAMPLE 26

Synthesis and Characterization of Phosphoramide IL 1

Phosphoramide appended IL 1

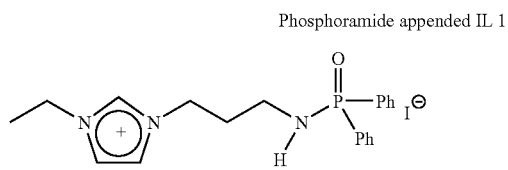

In a 250 mL flask charged with a magnetic stirbar and fitted with a reflux condenser, 10.0 g (80 mmol) 1-(3-aminopropyl) imidazole was dissolved in 60 mL dichloromethane. To this was added first 8.1 g (80 mmol) triethylamine, followed by 18.9 g of diphenylphosphinic chloride. The solution was heated to reflux overnight, after which time 60 mL of diethyl ether was added. The precipitated solids were removed by filtration, and the solvent evaporated from the filtrate. The residue was immediately redissolve in 100 mL of acetonitrile, and 12.6 g (excess) iodoethane added. The solution was stirred at 50° C. overnight, after which time the volatiles were removed in vacuo leaving a yellow oil (15.2 g). Characterization data: $^1$H NMR (300 MHz, CDCl$_3$, 25° C., TMS) δ 1.50 (t, 3H, CH$_3$), 2.22 (m, 2H, CH$_2$), 2.80 (br m, 1H), 3.01 (m, 2H, CH$_2$), 4.20 (q, 2H, CH$_2$), 4.55 (t, 2H, CH$_2$), 7.18–7.90 (overlapping m, 12H, CH), 10.02 (s, 1H, CH).

EXAMPLE 27

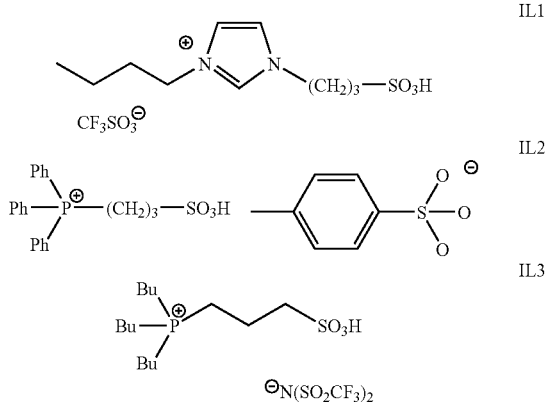

General Considerations

The starting materials N-butyl imidazole, triphenylphosphine, 1,4-butane-sultone and 1,3-propane-sultone were purchased from Aldrich. The starting material tributylphosphine was purchased from Cytec. The reagents trifluoromethane sulfonic acid (Aldrich), p-toluenesulfonic acid hydrate (Aldrich) and bis(trifluoromethanesulfonyl)imide (Rhodia) were purchased commercially. The solvents toluene (Fischer), acetonitrile (Fischer), and diethyl ether (Fischer) were used without further purification. The $^1$H NMR (300 MHz) and $^{13}$C NMR (75 MHz) spectra were obtained on a JOEL Eclipse 300 NMR spectrometer in D$_2$O. Chemical shifts were reported in parts per million (ppm, δ) and referenced to D$_2$O (δ 4.88).

Synthesis of IL1

To an acetonitrile solution (150 cm$^3$) of 1,4-butane sultone (47.83 g, 0.3513 mol), N-butyl imidazole (43.62 g, 0.3513 mol) was added in small portions. The mixture was heated and stirred at reflux overnight. The solution was concentrated in vacuo resulting in a solid zwitterion. The zwitterion was washed with diethyl ether (50 cm$^3$) and dried in vacuo with a rotary evaporator followed by overnight vacuum using a mechanical pump. 90.15 g of white solid zwitterion intermediate was obtained (98.6% yield). To a sample of the dried zwitterion (8.85 g, 0.03332 mol) neat trifluoromethane sulfonic acid (5.10 g, 0.03332 mol) was added. The mixture was stirred at room temperature for 12 hours, resulting in the formation of a viscous ionic liquid product (13.95 g, 100%). $^1$H NMR (300 MHz, D$_2$O); δ 8.68 (s, 1H), 7.40 (d, J=1.6, 1H), 7.39 (d, J=1.6, 1H), 4.13 (t, J=6.9, 2H), 4.08 (t, J=7.1, 2H), 2.82 (t, J=7.4, 2H), 1.91 (quint, J=8.0, 2H), 1.73 (q, J=7.7, 2H), 1.68–1.57 (m, 2H), 1.19 (dt, J=7.7, 7.7, 2H), 0.79 (t, J=7.4, 3H). $^{13}$C NMR (75.5 MHz, D$_2$O) δ 135.26, 122.64, 122.42, 119.80 (q, $J_{C-F}$=317.0, CF$_3$), 50.22, 49.49, 49.10, 31.31, 28.26, 21.11, 18.88, 12.75.

Synthesis of IL2

In a toluene solution (200 cm$^3$) of 1,3-propane sultone (19.80 g, 0.1621 mol) triphenylphosphine (42.52 g, 0.1621 mol) was added in small portions. The mixture was heated and stirred at reflux overnight. The solution was then concentrated in vacuo with a rotary evaporator. The resulting solid zwitterion was washed with diethyl ether (50 cm$^3$) and dried in vacuo with a rotary evaporator and mechanical pump (61.88 g, 99.3%). A portion of the dried zwitterion (3.47 g, 0.009034 mol) was acidified by the addition of solid p-toluenesulfonic acid hydrate (1.72 g, 0.009034 mol). The mixture of solids was warmed and stirred at 45° C.–60° C. overnight, resulting in the liquefaction of the solids; after cooling of the liquid the a stiff glass was formed that re-liquefies below 85° C. The presence of water (7–10 molecules per mole of salt) in the initial salt induces a lower melting point. The anhydrous salt melts at 180° C. $^1$H NMR (300 MHz, D$_2$O); δ 7.66–7.60 (m, 3H), 7.53–7.44 (m, 14H), 7.06 (d, J=8.0, 2H), 3.31–3.21 (m, 2H), 2.89 (t, J=6.9, 2H), 2.11 (s, 3H), 1.97–1.80 (m, 2H). $^{13}$C NMR (75.5 MHz, D$_2$O); δ 142.21, 139.75, 135.29, 135.25, 133.47, 133.34, 130.40, 130.23, 129.42, 125.44, 118.13, 116.98, 50.55, 50.33, 20.58, 20.04, 17.94.

Synthesis of IL3

In a toluene solution (10.0 cm$^3$) of tributylphosphine (50% by weight in toluene, 0.0222 mol) 1,3-propane sultone (2.72 g, 0.02227 mol) was added. The mixture was heated and stirred at reflux overnight under an argon atmosphere, resulting in the formation of a white precipitate. The solution was then concentrated in vacuo with a rotary evaporator to half it's original volume, and the solid product then isolated by filtration. The zwitterion was washed with diethyl ether (50 Cm$^3$) and dried in vacuo with a rotary evaporator and mechanical pump (4.77 g, 66%). The dried zwitterion (4.00 g, 0.0123 mol) was acidified by the addition of solid bis(trifluoromethanesulfonyl)imide (3.47 g, 0.0123 mol). The mixture was heated at 50° C. overnight under argon, resulting in the liquefaction of the solids and the formation of a somewhat viscous liquid (7.45 g, 99%) that decreases in viscosity even upon mild (45° C.) heating.

Synthesis of Ethyl Acetate Using an IL as Acid Catalyst

To IL2 (2.1 g, 4.0 mmol) was added via syringe acetic acid (1.0 mL, 17.5 mmol) and ethanol (1.0 mL, 17.5 mmol).

The reaction mixture was allowed to warm to a maximum temperature of 175° C. (external temperature) over a period of 45 min. Although completion of reaction was observed prior to reaching the maximum temperature, reuse of the reaction setup/IL made it necessary to remove all volatile components via distillation prior to the next cycle. With each cycle, reaction completion was confirmed by GC analysis [GC ((HP-1 methyl siloxane; f=1.0 mL/min) 50° C. (2 min), 10° C./min, 275° C. (10 min)) 3.21 min (EtOH), 3.37 min (EtOAC), 3.42 min (AcOH)] and documented via the mass of distillate obtained. Each cycle afforded pure ethyl acetate without any appreciable amounts of starting material (<7% assuming loss of EtOH due to an EtOH/EtOAc azeotrope (31% by weight and bp of 78° C.)). Biphasic mixtures were separated and factored into product formation was maximum water content of 3.3%.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A salt represented by 3:

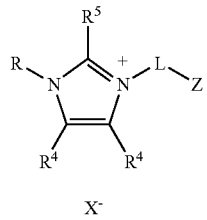

3 wherein
R represents independently for each occurrence alkyl, fluoroalkyl, cycloalkyl, aryl, heteroaryl, aralkyl, heteroaralkyl, or —(CH$_2$)$_n$—R$_8$;
R' represents independently for each occurrence H, alkyl, fluoroalkyl, aryl, heteroaryl, aralkyl, heteroarailcyl, formyl, acyl, alkyloxycarbonyl, aryloxycarbonyl, alkylaminocarbonyl, arylaminocarbonyl, or —(CH$_2$)$_n$—R$_8$;
R" represents independently for each occurrence H, alkyl, fluoroalkyl, aryl, heteroaryl, aralkyl, heteroaralkyl, or —(CH$_2$)$_n$—R$_8$;
R$^3$ represents independently for each occurrence H, F, or alkyl;
R$^4$ represents independently for each occurrence H, alkyl, fluoroalkyl, aryl, heteroaryl, aralkyl, heteroaralkyl, formyl, acyl, alkyloxycarbonyl, aryloxycarbonyl, alkylaminocarbonyl, arylaminocarbonyl, or —(CH$_2$)$_n$—R$_8$;
R$^5$ represents independently for each occurrence H, alkyl, fluoroalkyl, aryl, heteroaryl, aralkyl, heteroaralkyl, or —(CH$_2$)$_n$—R$_8$;
L represents (C(R$^3$)$_2$)$_n$, (C(R$^3$)$_2$)$_n$J(C(R$^3$)$_2$)$_m$, or (C(R$^3$)$_2$)$_n$Ar(C(R$^3$)$_2$)$_m$;
Z represents —SO$_3$H, —CO$_2$H, —CO$_2$R, —C(O)N(R")$_2$, —C(O)N(R")N(R")$_2$, —N(R')$_2$, —OR', —SR', —S(O)R", —S(O)$_2$R", —CN, —N(R")P(O)(R)$_2$, —C(OR')(R")$_2$, alkenyl, or alkynyl;
Ar represents independently for each occurrence aryl or heteroaryl;
J represents independently for each occurrence O, S, NR', cycloalkyl, or heterocyclyl;
X$^-$ represents phosphorus tetrafluoride, alkylsulfonate, fluoroalkylsulfonate, arylsulfonate, bis(alkylsulfonyl)amide, bis(fluoroalkylsulfonyl)amide, bis(arylsulfonyl)amide, (fluoroalkylsulfonyl)(fluoroalkylcarbonyl)amide, nitrate, nitrite, sulfate, hydrogensulfate, alkyl sulfate, aryl sulfate, carbonate, bicarbonate, carboxylate, phosphate, hydrogen phosphate, dihydrogen phosphate, hypochlorite, or an anionic site of a cation-exchange resin;
R$^8$ represents independently for each occurrence cycloalkyl, aryl, or heteroaryl;
m represents independently for each occurrence an integer in the range 1–10 inclusive; and
n represents independently for each occurrence an integer in the range 1–10 inclusive.

2. The salt of claim 1, wherein R represents independently for each occurrence alkyl.

3. The salt of claim 1, wherein R$^4$ represents independently for each occurrence H or alkyl.

4. The salt of claim 1, wherein R$^5$ represents independently for each occurrence H or alkyl.

5. The salt of claim 1, wherein R$^5$ represents independently for each occurrence alkyl.

6. The salt of claim 1, wherein Z represents —SO$_3$H or —N(R')$_2$.

7. The salt of claim 1, wherein L represents (C(R$^3$)$_2$)$_n$.

8. The salt of claim 1, wherein X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

9. The salt of claim 1, wherein X$^-$ represents bis(methanesulfonyl)amide, bis(trifluoromethanesulfonyl)amide, bis(benzenesulfonyl)amide, or bis(p-toluenesulfonyl)amide.

10. The salt of claim 1, wherein X$^-$ represents bis(trifluoromethanesulfonyl)amide or (trifluoromethanesulfonyl)(trifluoroacetyl)amide.

11. The salt of claim 1, wherein R represents independently for each occurrence alkyl; and Z represents —SO$_3$H or —N(R')$_2$.

12. The salt of claim 1, wherein R represents independently for each occurrence alkyl; Z represents —SO$_3$H or —N(R')$_2$; and L represents (C(R$^3$)$_2$)$_n$.

13. The salt of claim 1, wherein R represents independently for each occurrence alkyl; Z represents —SO$_3$H or —N(R')$_2$; L represents (C(R$^3$)$_2$)$_n$; and X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide.

14. The salt of claim 1, wherein R represents independently for each occurrence alkyl; Z represents —SO$_3$H or —N(R')$_2$; L represents (C(R$^3$)$_2$)$_n$; and X$^-$ represents bis(methanesulfonyl)amide, bis(trifluoromethanesulfonyl)amide, bis(benzenesulfonyl)amide, or bis(p-toluenesulfony)amide.

15. The salt of claim 1, wherein R represents independently for each occurrence alkyl; Z represents —SO$_3$H or —N(R')$_2$; L represents (C(R$^3$)$_2$)$_n$; and X$^-$ represents bis(trifluoromethanesulfonyl)amide or (trifluoromethanesulfonyl)(trifluoroacetyl)amide.

16. The salt of claim 1, wherein R represents independently for each occurrence alkyl; Z represents —SO$_3$H or —N(R')$_2$; L represents (C(R$^3$)$_2$)$_n$; X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; and R$^4$ represents independently for each occurrence H or alkyl.

17. The salt of claim 1, wherein R represents independently for each occurrence alkyl; Z represents —SO$_3$H or —N(R')$_2$; L represents (C(R$^3$)$_2$)$_n$; X$^-$ represents bis(methanesulfonyl)amide, bis(trifluoromethanesulfonyl)amide, bis(benzenesulfonyl)amide, or bis(p-toluenesulfonyl)amide; and R$^4$ represents independently for each occurrence H or alkyl.

18. The salt of claim 1, wherein R represents independently for each occurrence alkyl; Z represents —SO$_3$H or —N(R')$_2$; L represents (C(R$^3$)$_2$)$_n$; X$^-$ represents bis(trifluoromethanesulfonyl)amide; and R$^4$ represents independently for each occurrence H or alkyl.

19. The salt of claim 1, wherein R represents independently for each occurrence alkyl; Z represents —SO$_3$H or —N(R')$_2$; L represents (C(R$^3$)$_2$)$_n$; X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; R$^4$ represents independently for each occurrence H or alkyl; and R$^5$ represents independently for each occurrence H or alkyl.

20. The salt of claim 1, wherein R represents independently for each occurrence alkyl; Z represents —SO$_3$H or —N(R')$_2$; L represents (C(R$^3$)$_2$)$_n$; X$^-$ represents bis(methanesulfonyl)amide, bis(trifluoromethanesulfonyl)amide, bis(benzenesulfonyl)amide, or bis(p-toluenesulfonyl)amide; R$^4$ represents independently for each occurrence H or alkyl; and R$^5$ represents independently for each occurrence H or alkyl.

21. The salt of claim 1, wherein R represents independently for each occurrence alkyl; Z represents —SO$_3$H or —N(R')$_2$; L represents (C(R$^3$)$_2$)$_n$; X$^-$ represents bis(trifluoromethanesulfonyl)amide; R$^4$ represents independently for each occurrence H or alkyl; and R$^5$ represents independently for each occurrence H or alkyl.

22. The salt of claim 1, wherein R represents independently for each occurrence alkyl; Z represents —SO$_3$H or —N(R')$_2$; L represents (C(R$^3$)$_2$)$_n$; X$^-$ represents methanesulfonate, trifluoromethanesulfonate, benzenesulfonate, p-toluenesulfonate, bis(methanesulfonyl)amide, bis(trifluoromethanesulfonyl)amide, bis(benzenesulfonyl)amide, or bis(p-toluenesulfonyl)amide; R$^4$ represents independently for each occurrence H or alkyl; and R$^5$ represents independently for each occurrence alkyl.

23. The salt of claim 1, wherein R represents independently for each occurrence alkyl; Z represents —SO$_3$H or —N(R')$_2$; L represents (C(R$^3$)$_2$)$_n$; X$^-$ represents bis(methanesulfonyl)amide, bis(trifluoromethanesulfonyl)amide, bis(benzenesulfonyl)amide, or bis(p-toluenesulfonyl)amide; R$^4$ represents independently for each occurrence H or alkyl; and R$^5$ represents independently for each occurrence alkyl.

24. The salt of claim 1, wherein R represents independently for each occurrence alkyl; Z represents —SO$_3$H or —N(R')$_2$; L represents (C(R$^3$)$_2$)$_n$; X$^-$ represents bis(trifluoromethanesulfonyl)amide; R$^4$ represents independently for each occurrence H or alkyl; and R$^5$ represents independently for each occurrence alkyl.

* * * * *